(12) United States Patent  
Mattern

(10) Patent No.: US 8,784,882 B2  
(45) Date of Patent: *Jul. 22, 2014

(54) CONTROLLED RELEASE DELIVERY SYSTEM FOR NASAL APPLICATIONS AND METHOD OF TREATMENT

(75) Inventor: Claudia Mattern, Stans (CH)

(73) Assignee: Mattern Pharma AG, Vaduz (LI)

( * ) Notice: Subject to any disclaimer, the term of this patent is extended or adjusted under 35 U.S.C. 154(b) by 0 days.

This patent is subject to a terminal disclaimer.

(21) Appl. No.: 13/194,853

(22) Filed: Jul. 29, 2011

(65) Prior Publication Data

US 2012/0058176 A1 Mar. 8, 2012

Related U.S. Application Data

(60) Continuation of application No. 12/796,165, filed on Jun. 8, 2010, now abandoned, which is a division of application No. 11/560,187, filed on Nov. 15, 2006, now abandoned, which is a continuation-in-part of application No. 10/772,964, filed on Feb. 4, 2004, now abandoned.

(30) Foreign Application Priority Data

Nov. 11, 2003 (EP) .................................... 03025769

(51) Int. Cl.
*A61K 9/127* (2006.01)
*A61K 31/56* (2006.01)
*A61F 13/00* (2006.01)

(52) U.S. Cl.
USPC .......................... 424/450; 424/434; 514/179

(58) Field of Classification Search
USPC .................................. 424/450, 434; 514/179
See application file for complete search history.

(56) References Cited

U.S. PATENT DOCUMENTS

| 4,071,623 A | | 1/1978 | van der Vies |
| 4,083,973 A | * | 4/1978 | van der Vies ................ 514/178 |
| 4,315,925 A | | 2/1982 | Hussain et al. |
| 4,581,225 A | | 4/1986 | Su et al. |
| 4,752,425 A | * | 6/1988 | Martin et al. .................. 264/4.6 |

(Continued)

FOREIGN PATENT DOCUMENTS

| DE | 943792 | 6/1956 |
| DE | 1569286 | 10/1976 |

(Continued)

OTHER PUBLICATIONS

Ko et al. (Journal of Microencapsulation 1998, vol. 15, No. 2, pp. 197-205).*

(Continued)

*Primary Examiner* — Aradhana Sasan
(74) *Attorney, Agent, or Firm* — Foley & Lardner LLP

(57) ABSTRACT

This invention relates to a gel formulation for nasal administration of a controlled release formulation of hormones to the systemic circulation and/or to the brain. The special lipophilic or partly lipophilic system of the invention leads to higher bioavailability of the active ingredient caused by sustained serum levels in plasma but also leads to a more favorable serum level profile. The special lipophilic or partly lipophilic system also allows for the modulation of brain functioning. The invention also relates to the nasal administration of steroid hormones for treatment of female sexual dysfunction (FSD) or female arousal disorder.

55 Claims, 14 Drawing Sheets

(56) References Cited

U.S. PATENT DOCUMENTS

| | | | |
|---|---|---|---|
| 5,049,387 A | | 9/1991 | Amkraut |
| 5,397,771 A | * | 3/1995 | Bechgaard et al. ............ 514/9.7 |
| 5,455,286 A | | 10/1995 | Amidon et al. |
| 5,514,673 A | | 5/1996 | Heckenmuller et al. |
| 5,635,203 A | | 6/1997 | Gale et al. |
| 5,645,856 A | * | 7/1997 | Lacy et al. .................... 424/455 |
| 5,747,058 A | | 5/1998 | Tipton et al. |
| 5,756,071 A | * | 5/1998 | Mattern et al. .................. 424/45 |
| 5,863,554 A | | 1/1999 | Illum et al. |
| 5,877,216 A | * | 3/1999 | Place et al. .................... 514/573 |
| 5,897,894 A | | 4/1999 | Glass |
| 6,248,363 B1 | * | 6/2001 | Patel et al. .................... 424/497 |
| 6,287,588 B1 | | 9/2001 | Shih et al. |
| 6,310,089 B1 | | 10/2001 | Watts et al. |
| 6,432,440 B1 | | 8/2002 | Watts et al. |
| 6,451,339 B2 | | 9/2002 | Patel et al. |
| 6,720,001 B2 | | 4/2004 | Chen et al. |
| 6,761,903 B2 | | 7/2004 | Chen et al. |
| 6,833,478 B2 | | 12/2004 | Bottaro et al. |
| 6,958,142 B2 | | 10/2005 | Daniels et al. |
| 7,186,706 B2 | | 3/2007 | Rosario-Jansen et al. |
| 2001/0055569 A1 | | 12/2001 | Davis et al. |
| 2002/0136752 A1 | * | 9/2002 | Whittle et al. ................. 424/435 |
| 2002/0198136 A1 | | 12/2002 | Mak et al. |
| 2004/0005275 A1 | * | 1/2004 | Gizurarson et al. ............ 424/45 |
| 2005/0100564 A1 | | 5/2005 | Mattern |
| 2005/0153946 A1 | | 7/2005 | Hirsh et al. |
| 2005/0187188 A1 | | 8/2005 | Stein et al. |
| 2006/0147385 A1 | | 7/2006 | Pike et al. |
| 2006/0210622 A1 | | 9/2006 | Pace et al. |
| 2006/0211664 A1 | | 9/2006 | Dudley |
| 2007/0149454 A1 | | 6/2007 | Mattern |
| 2009/0227550 A1 | | 9/2009 | Mattern |
| 2010/0311707 A1 | | 12/2010 | Mattern |
| 2011/0009318 A1 | | 1/2011 | White et al. |
| 2011/0245215 A1 | | 10/2011 | Carrara et al. |
| 2012/0009249 A1 | | 1/2012 | Mattern |
| 2012/0009250 A1 | | 1/2012 | Mattern |
| 2012/0083480 A1 | * | 4/2012 | Mattern ........................ 514/178 |
| 2012/0277202 A1 | | 11/2012 | Mattern |
| 2012/0297730 A1 | | 11/2012 | Mattern |

FOREIGN PATENT DOCUMENTS

| | | | |
|---|---|---|---|
| EP | 0 160 501 | | 11/1985 |
| EP | 0349091 | | 1/1990 |
| GB | 1 569 286 | | 6/1980 |
| GB | 2 237 510 | | 5/1991 |
| JP | 01016716 | * | 1/1989 ............ A61K 47/24 |
| JP | 2003/509453 | | 3/2003 |
| TW | 175318 | | 12/1991 |
| WO | WO 95/20945 A1 | | 8/1995 |
| WO | WO 97/40823 | | 11/1997 |
| WO | WO 00/59512 | | 10/2000 |
| WO | WO 01/41732 A1 | | 6/2001 |
| WO | WO 01/95888 A1 | | 12/2001 |
| WO | WO 03/063833 A1 | | 8/2003 |

OTHER PUBLICATIONS

Office Action issued on Jan. 13, 2012 by the Examiner in U.S. Appl. No. 12/796,165 (US 2010/0311707).
Office Action issued on Nov. 16, 2009 by the Examiner in U.S. Appl. No. 11/560,187 (US 2007/0149454).
Office Action issued on Mar. 18, 2009 by the Examiner in U.S. Appl. No. 11/560,187 (US 2007/0149454).
Office Action issued on Oct. 29, 2008 by the Examiner in U.S. Appl. No. 11/560,187 (US 2007/0149454).
Office Action issued on Aug. 20, 2008 by the Examiner in U.S. Appl. No. 11/560,187 (US 2007/0149454).
Office Action issued on Feb. 5, 2008 by the Examiner in U.S. Appl. No. 11/560,187 (US 2007/0149454).
Office Action issued on Sep. 14, 2007 by the Examiner in U.S. Appl. No. 11/560,187 (US 2007/0149454).
Office Action issued on Jul. 8, 2010 by the Examiner in U.S. Appl. No. 10/772,964 (US 2005/0100564).
Office Action issued on Sep. 29, 2009 by the Examiner in U.S. Appl. No. 10/772,964 (US 2005/0100564).
Office Action issued on Jan. 15, 2009 by the Examiner in U.S. Appl. No. 10/772,964 (US 2005/0100564).
Office Action issued on May 5, 2008 by the Examiner in U.S. Appl. No. 10/772,964 (US 2005/0100564).
Office Action issued on Mar. 17, 2008 by the Examiner in U.S. Appl. No. 10/772,964 (US 2005/0100564).
Office Action issued on Apr. 4, 2007 by the Examiner in U.S. Appl. No. 10/772,964 (US 2005/0100564).
Office Action issued on Jul. 3, 2012 by the Examiner in U.S. Appl. No. 13/316,494 (US 2012/0083480).
Office Action issued on Oct. 19, 2012 by the Examiner in U.S. Appl. No. 13/567,878 (US 2012/0297730)).
Office Action issued on Nov. 5, 2012 by the Examiner in U.S. Appl. No. 13/194,928 (US 2012/0009250).
Office Action issued on Feb. 15, 2012 by the Examiner in U.S. Appl. No. 13/194,928 (US 2012/0009250).
Office Action issued on Nov. 9, 2011 by the Examiner in U.S. Appl. No. 13/194,928 (US 2012/0009250).
International Search Report issued on Dec. 21, 2007 in U.S. Appl. No. PCT/EP2007/008409 (corresponding to US 2012/0009249).
Mattern et al., "Testosterone supplementation for hypogonadal men by the nasal route," The Aging Male, vol. 11, No. 4, pp. 171-178, Dec. 2008.
Banks et al., "Delivery of testosterone to the brain by intranasal administration: Comparison to intravenous testosterone," Journal of Drug Targeting, vol. 17, No. 2, pp. 1-7, Dec. 16, 2008.
Danner et al., "Androgen Substitution with Testosterone Containing Nasal Drops," International Journal of Andrology, vol. 3, No. 4, pp. 429-435, 1980.
Jung et al., "Prolonged delivery of nicotine in rats via nasal administration of proliposomes," Journal of Controlled Release, vol. 66, pp. 73-79, 2000.
Ohman et al., "17β-Estradiol Levels in Blood and Cerebrospinal Fluid After Ocular and Nasal Administration in Women and Female Rhesus Monkeys (*Macaca mulatta*)," Contraception, vol. 22, No. 4, pp. 349-358, Oct. 1980.
Skipor et al., "Local transport of testosterone from the nasal mucosa to the carotid blood and the brain in the pig," Polish Veterinary Sciences, vol. 3, No. 1, pp. 19-22, 2000.
Hussain et al., "Intranasal Drug Delivery," Advanced Drug Delivery Reviews, vol. 29, pp. 39-49, 1998.
Kumar et al., "Pharmacokinetics of progesterone after its administration to ovariectomized rhesus monkeys by injection, infusion, or nasal spraying," Proc. Natl. Acad. Sci. USA, vol. 79, pp. 4185-4189, Jul. 1982.
David et al., "Bioavailability of progesterone enhanced by intranasal spraying," Experientia, vol. 37, pp. 533-534, 1981.
Wattanakumtornkul et al., "Intranasal hormone replacement therapy," Menopause: The Journal of the North American Menopause Society, vol. 10, No. 1, pp. 88-98, 2003.
Hussain et al., "Nasal Absorption of Propranolol from Different Dosage Forms by Rats and Dogs," Journal of Pharmaceutical Sciences, vol. 69, No. 12, pp. 1411-1413, Dec. 1980.
Patent Abstracts of Japan, Tanabe Seiyaku Co., Ltd., "Dopamine Nasal Administration Preparation," JP 01-160916, Jun. 23, 1989.
European Search Report issued on Apr. 22, 2004 in application No. EP 03 02 5769.
International Search Report issued on Mar. 31, 2005 in application No. PCT/EP2004/012122.
Taiwanese Search Report issued Jan. 2006 in application No. 093129982.
Mattern et al., "Development of a drug formulation for nasal administration of a testosterone precursor and test of its bioavailability," First World Congress on Aging Male, Geneva, Switzerland, 1998, Abstract.
Häcker et al., "Androgenic substitution for the ageing male by nasal administraton of a precursor of testosterone," First World Congress on Aging Male, Geneva, Switzerland, 1998, Abstract.

(56) References Cited

OTHER PUBLICATIONS

Müller et al., "Androgenic deficiencies of the ageing male and psychophysiological performance—test system for clinical diagnosis," First World Congress on Aging Male, Geneva, Switzerland, 1998, Abstract.

Nogueira et al., "In-Vivo monitoring of neostriatal dopamine activity after nasal drug administration in the rat: relevance to Parkinson's Disease and addiction," Neuroscience Meeting, San Diego, California, 1995, Abstract.

Topic et al., "Evidence for antidepressant-like action of intranasal application of testosterone," CINP Biennial International Congress, Munich, Germany, Jul. 13-17, 2008, Abstract.

Provasi et al., "Nasal delivery progesterone powder formulations comparison with oral administration," Bol. Chim. Farmaceutico, Anno 132—n. 10 poster, 1993.

Corbo et al., "Nasal delivery of progestational steroids in ovariectomized rabbits. II. Effect of penetrant hydrophilicity," International Journal of Pharmaceutics, vol. 50, pp. 253-260, 1989.

Cicnelli et al., "Nasally-administered progesterone: comparison of ointment and spray formulations," Maturitas, vol. 13, pp. 313-317, 1991.

Cicinelli et al., "Administration of unmodified progesterone by nasal spray in fertile women," Gynecol. Endocrinol., vol. 9, pp. 289-293, 1995.

Dondeti et al., "Bioadhesive and formulation parameter affecting nasal absorption", International Journal of Pharmaceutics, 127 (1996) 115-133.

Hussain et al., "Testosterone 1713-N, N-Dimethylglycinate Hydrochloride: A Prodrug with a Potential for Nasal Delivery of Testosterone", Journal of Pharmaceutical Sciences, vol. 91, No. 3, Mar. 2002, pp. 785-789.

Cicinelli et al., "Progesterone administration by nasal spray", Fertility and Sterility, vol. 56, No. 1, Jul. 1991, pp. 139-141.

Cicinelli et al., "Progesterone administration by nasal spray in menopausal women: comparison between two different spray formulations", Gynecol. Endocrinol., 6(1992), pp. 247-251.

Cicinelli et al., "Nasal spray administration of unmodified progesterone: evaluation of progesterone serum levels with three different radioimmunossay techniques", Maturitas Journal of the Climacteric & Postmenopause, 19(1994), pp. 43-52.

Steege et al., "Bioavailability of nasally administered progesterone", Fertility and Sterility, vol. 46, No. 4, 1986, pp. 727-729.

Notice of Allowance issued on Jul. 5, 2013 by the Examiner in U.S. Appl. No. 13/194,928 (US 2012/0009250).

Notice of Allowance issued on Mar. 25, 2013 by the Examiner in U.S. Appl. No. 13/194,928 (US 2012/0009250).

Office Action issued on Mar. 22, 2013 by the Examiner in U.S. Appl. No. 13/316,494 (US 2012/0083480).

* cited by examiner

CONTROLLED RELEASE DELIVERY SYSTEM FOR NASAL APPLICATIONS AND METHOD OF TREATMENT

CROSS-REFERENCE TO RELATED APPLICATIONS

The present application is a continuation of U.S. patent application Ser. No. 12/796,165, filed Jun. 8, 2010, which is a divisional of U.S. patent application Ser. No. 11/560,187, filed Nov. 15, 2006, which is a continuation-in part of U.S. patent application Ser. No. 10/772,964 filed Feb. 4, 2004, which claims priority to European Patent Application No. 03025769.5, filed Nov. 11, 2003. The contents of each of the foregoing applications are hereby incorporated by reference in their entirety.

FIELD OF THE INVENTION

The invention relates generally to a formulation for the controlled release of hormones to the systemic circulation and/or to the brain (by bypassing the blood-brain barrier) after nasal application and for the modulation of brain functioning. More specifically, the invention relates to the treatment of neuroendocrinologic disorders, such as Female Sexual Disorder (FSD) by nasally administering a formulation comprising a hormone drug.

BACKGROUND

A growing body of evidence suggests a modulatory role of brain-acting compounds, such as neurosteroids (e.g., androgens, progestins) or neurotransmitters in the regulation of disorders influenced by receptors in the brain, such as depression, Parkinson's disease, Alzheimer's, or even loss of libido.

Considerable importance has been placed on the measurement of receptor concentrations in the brain. However, the underlying mechanisms of action are still poorly understood. Much of the confusion about the wide range of effects and side effects is due to various non-genomic actions. Tissues traditionally considered non-targets for clinical action are today found to be vividly regulated by non-genomic mechanisms.

Generally, genomic actions are typically due to compounds binding to intracellular receptors, traveling to the nucleus of the cell, and binding to DNA to initiate expression of various proteins. These various proteins exert a wide range of effects. The compounds may also induce transcription-independent signaling, thus modulating non-genomic responses. These second messenger pathways involve kinase pathways, including ion flux as well as cAMP or lipase. In contrast to the genomic effects, most of the non-genomic effects are immediate.

Thus, the mechanisms mediating the effects of a molecule can be both genomic and non-genomic. The clinical relevance of the genomic effects often is understood. However, there is very little knowledge of the possible differential relevance of a molecule's non-genomic actions in different cell types. It is hypothesized that non-genomic signaling mechanisms might be more of a pharmacological phenomenon. At the very best, these can be influenced by the way a molecule is administered.

Nasal drug delivery offers many advantages that include rapid adsorption due to the abundant presence of capillary vessels in the nose, fast onset of action, avoidance of hepatic first-pass metabolism, utility for chronic medication, and ease of administration. It is also known that, in contrast to large and/or ionized molecules, lipophilic pharmaceutical compounds having a sufficiently low molecular weight generally are readily absorbed by the mucous membrane of the nose. For such drugs, it is possible to obtain pharmacokinetic profiles similar to those obtained after intravenous injection.

However, maintaining constant in vivo therapeutic drug concentrations for an extended period of time has been problematic. The rapid mucociliary clearance of a therapeutic agent from the site of deposition and the presence of enzymes in the nasal cavity (that may cause degradation of the therapeutic agent) result in a short time span available for absorption.

Many efforts have been made in the art in attempt to overcome these limitations. GB 1987000012176 describes the use of bioadhesive microspheres to increase residence time in the nasal cavity. It has also been found that the use of enhancers improves permeability of the nasal membrane and stabilizers prevent drug degradation. PCT/GB98/01147 (U.S. Pat. No. 6,432,440) describes the use of in situ gelling pectin formulations.

Investigations on the nasal absorption of sexual steroids, which are rather small and lipophilic compounds, have shown that sexual steroids are readily absorbed by the mucous membrane of the nose and are found very quickly in serum. Due to this fact, the short half-life of sexual steroids, and the limited possibilities for formulating nasal application forms with sustained release, the use of sexual steroids in clinical practice has been limited because hormone replacement therapy, in general, is a long-term application.

Several formulations have been proposed for sexual steroid drugs. Testosterone is nearly water-insoluble and somewhat more soluble in vegetable oil. Hussain et al., J. Pharm. Sci. 91(3): 785-789 (2002), concluded that testosterone would be an ideal candidate for nasal administration if its solubility in water could be increased. Hussain et al. proposed using a water-soluble pro-drug, testosterone 17β-N,N-dimethylglycinate, and found serum levels equal to intravenous administration with peak plasma concentrations within twelve minutes (25 mg dose) and twenty minutes (50 mg dose) and elimination half-lives of about fifty-five minutes. It should be noted, however, that this speed is not necessary or desirable because sex hormone replacement is not an emergency therapy.

Ko et al., J. Microencaps., 15(2): 197-205 (1998), proposed the use of charged testosterone submicron O/W emulsion formulations (water/Tween80, soybean oil/Span80) based on the hypothesis that increased absorption is possible upon solubilization of the drug and/or prolongation of the formulation residence time in the nose. Ko et al. found higher relative bioavailability for the positively (55%) and negatively (51%) charged emulsions compared to the neutral one (37%). $T_{max}$ was observed in every case at about twenty minutes after administration. However, because Ko et al. did not take blood samples before application, it is not possible to evaluate the differences in the decrease of serum levels, although from a graph it seems that after intravenous application (hydroalcoholic solution) the level shows the longest elimination half time. In practice, however, such an emulsion is not suitable for nasal application because of the droplet size (approximately 430 nm).

The solubility of progesterone in water and oil is somewhat comparable to that of testosterone but investigators have taken different approaches. It has been that progesterone dissolved in almond oil (20 mg/ml) and administered by nasal spray lead to higher bioavailability than that provided by progesterone dissolved in dimethicone or a PEG-based ointment (Fertil Steril 56(1): 139-141 (1991); Maturitas 13(4):

313-317 (1991); Gynecol Endocrinol 6(4): 247-251 (1992); Fertil Steril, 60(6): 1020-1024 (1993); and Maturitas 19(1): 43-52 (1994)).

After nasal application of progesterone in almond oil, $C_{max}$ levels were observed after thirty to sixty minutes, decreasing significantly six to eight hours after a single administration. Steege et al., Fertil Steril, 46(4): 727-729 (1986), dissolved progesterone in polyethylene glycol (200 mg/ml) and found $T_{max}$ at thirty minutes. The duration of serum levels was at least eight hours but with high variations. When progesterone was formulated in ethanol/propylene glycol/water, however, $T_{max}$ was at only 5.5 minutes (Kumar et al, Proc. Natl. Acad. Sci. U.S.A., 79: 4185-9 (1982)). Provasi et al., Boll. Chim. Farm. 132(10): 402-404 (1993), investigated powder mixtures (co-ground and co-lyophilized progesterone/cyclodextrin) containing progesterone. Provasi et al. found $T_{max}$ at within two to five minutes with serum levels decreasing after only twenty minutes.

The results for progesterone described above are quite similar to that found for testosterone and for an already marketed aqueous nasal spray containing estradiol, formulated in cyclodextrin (commercially available as AERODIOL® from Servier Laboratories, France). Maximum plasma levels are reached within ten to thirty minutes and decrease to 10% of the peak value after two hours. Again, this speed is not necessary for sex hormone replacement therapy and is not desirable in view of the short elimination half-life of hormones.

Apart from the "liberation/adsorption" problem shown above in connection with sexual hormones and bioavailability, the focus of research has centered on the crucial liver metabolism and the short half-life of the compounds. However, high protein-binding also presents a problem because only the unbound fraction is biologically active. Approximately 40% of circulating plasma testosterone binds to sex hormone binding globulin (SHBG)—2% in men and up to 3% in women remains unbound (free)—and the remainder binds to albumin and other proteins. The fraction bound to albumin dissociates easily and is presumed to be biologically active, whereas the SHBG fraction is not. It should be noted that the amount of SHBG in plasma determines the distribution of testosterone in free and bound forms, whereas free testosterone concentrations determine (limit) the drug's half-life.

Additional research has shown that pharmacokinetics (and the resulting efficacy) may be determined by the route of testosterone administration. Previous research has shown that sublingual application of testosterone undecanoate results in a very fast and high testosterone peak that triggers sexual arousal. Apperloo et al., J Sex Med, 3:541-549 (2006), recently found that a single dose of a vaginally-applied testosterone propionate results in a slower rising and lower testosterone peak that does not trigger sexual arousal. Apperloo et al. found an acute and prolonged rise in testosterone and free testosterone above physiological levels with a peak at 5.5 hours is not sufficient to influence the female sexual response. Recently, it was hypothesized that some effects of hormones are typically mediated by their neurobiological activity. Thus, these application forms probably lack a sufficient CNS effect. In order to achieve a corresponding efficacy, the therapeutic agent has to cross the blood-brain barrier. The therapeutic agent, however, not only has to cross the blood-brain barrier in a certain concentration, it additionally has to stay in the brain long enough to exert its desired action.

Accordingly, there has remained a need for a sexual hormone drug formulation system that is therapeutically effective when administered to the nose of a patient and is safe, stable and easily manufactured.

SUMMARY OF THE INVENTION

The inventor has surprisingly found that the incorporation of various hormone drugs, such as sexual hormones, into a special lipophilic or partly lipophilic system not only leads to a higher bioavailability in general caused by sustained serum levels in plasma but also to a more favorable serum level profile. In an especially important aspect, the lipophilic or partly lipohilic system of the invention allows hormones to cross the blood-brain-barrier in such a way as to achieve efficacy in medicines for disorders of the central nervous system (CNS).

The invention comprises a formulation for nasal application comprising: (a) at least one active ingredient; (b) at least one lipophilic or partly lipophilic carrier; and (c) a compound or a mixture of compounds having surface tension decreasing activity in an amount effective for in situ generation of an emulsion upon contact of the formulation with water.

While not wishing to be bound by theory, it is believed that nasal administration of the formulation of the invention may be able to recruit selective actions of a molecule which, in turn, may provide new clinical applications. Of particular interest is the use of formulations to modulate brain functioning. Application of the formulation of the invention to the nose results in surprising and different action of compounds to the brain as compared to what is seen with conventional formulations. While not wishing to be bound by theory, it is believed that this effect is due to new, possibly also non-genomic, mechanisms that are made available by the gel formulation of the invention.

DETAILED DESCRIPTION OF THE INVENTION

Figure 1:
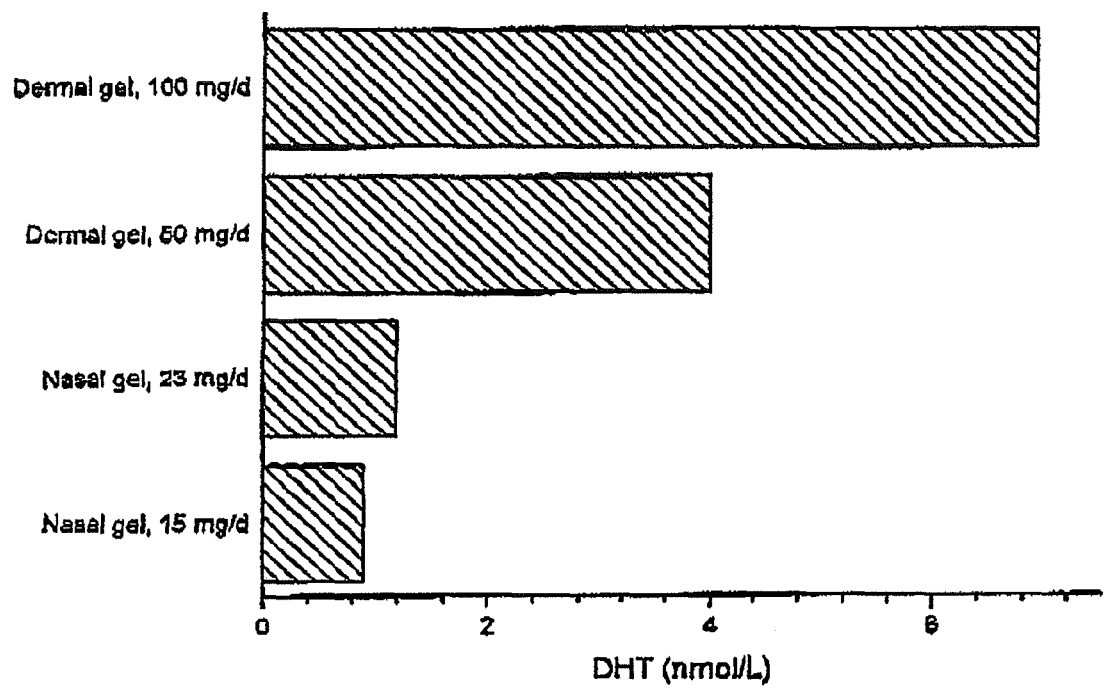
FIG. 1 shows a comparison of DHT levels after application of different doses of testosterone as a dermal or nasal gel to hypogonadal men.

The formulation of the invention is chemically and physically stable and can be in the form of a suspension or a solution of the pharmacologically active substance. The formulation of the invention may be filled into a preservative-free device able to accurately deliver doses of the above formulation, even at higher viscosities.

After nasal application of the formulation of the invention, the active ingredient or active ingredient particles are efficiently trapped at the deposition site and are absorbed at a predictable rate across the mucous membrane of the patient, thereby limiting possible deactivation by metabolizing enzymes and/or protein-binding.

It will also be understood that the terms and expressions used herein have the ordinary meaning as is accorded to such terms and expressions with respect to their corresponding respective areas of inquiry and study except where specific meanings have otherwise been set forth herein.

The term "higher availability" shall mean that after a single application a serum level of hormone significantly higher than baseline is maintained for six hours, more preferably for eight hours and most preferably for at least ten hours. The term "higher availability" shall also mean that, after a single application, a cerebral spinal fluid (CSF) level significantly higher than baseline can be achieved and maintained long enough to exert the desired action.

The term "hormone" shall mean polypeptide hormones, oligopeptide hormones, amine hormones, steroid hormones (such as sexual hormones, including testosterone), and lipid and phospholipids-derived hormones.

The term "sexual hormone drug" shall mean a sexual hormone (such as testosterone), a biologic pro-drug of a sexual hormone (such as androstenedione, progesterone, 17-α-hydroxyprogesterone), a derivative of a sexual hormone (such as mestanolone and 4-chloro-1-dehydromethyltestosterone), or a combination thereof.

The inventive formulation for nasal application comprises (a) at least one active ingredient; (b) at least one lipophilic or partly lipophilic carrier; and (c) a compound or mixture of compounds having surface tension decreasing activity in an amount effective for in situ generation of an emulsion upon contact of the formulation with water.

The active ingredient is generally a hormone drug. Preferably, the hormone drug is comprised within the formulation in an amount up to about 0.2 to about 6% by weight, preferably 0.2 to 4% by weight. In one aspect of the invention, the hormone drug is a sexual hormone drug. Preferably, the sexual hormone drug is testosterone.

In one aspect, the active ingredient may be introduced into the formulation in a processed form, such as nano- or micro-particles, liposomes, bilayer vesicles, and micelles, among others.

The formulation of the invention also comprises at least one lipophilic or partly lipophilic carrier. The formulation of the invention comprises oil in a range of about 30% to about 98% by weight, preferably about 60 to about 98% by weight, more preferably about 75% to about 95% by weight, even more preferably about 85% to about 95% by weight, and most preferably about 90% by weight. In a preferable aspect, the lipophilic carrier comprises an oil or a mixture of oils, such as a vegetable oil, such as castor oil, soybean oil, sesame oil, or peanut oil, fatty acid esters such as ethyl- and oleyloleat, isopropylmyristate, medium chain triglycerides, glycerol esters of fatty acids, or polyethylene glycol, phospholipids, white soft paraffin, hydrogenated castor oil, or a mixture thereof. More preferably, the oil is a vegetable oil. Most preferably, the oil is castor oil. In one aspect, the lipophilic carrier may comprise a mixture of oils. In a preferable aspect, the vegetable oil is castor oil.

The formulation of the invention also comprises a compound or mixture of compounds having surface tension decreasing activity in an amount effective for in situ generation of an emulsion upon contact of the formulation with water in an amount of about 1 to about 20% by weight, preferably about 1 to about 10% by weight, more preferably about 1 to about 5% by weight, and most preferably at about 4% by weight. The surface tension decreasing component generally comprises at least one surfactant selected from the group consisting of anionic, cationic, amphoteric, and nonionic surfactants, including, but not limited to, lecithin, fatty acid ester of polyvalent alcohols, fatty acid ester of sorbitanes, fatty acid ester of polyoxyethylensorbitans, fatty acid ester of polyoxyethylene, fatty acid ester of sucrose, fatty acid ester of polyglycerol, oleoyl macrogolglycerides, and/or at least one humectant such as sorbitol, glycerine, polyethylene glycol, macrogol glycerol fatty acid ester, or mixture thereof. Preferably, the surface tension decreasing component is an oleoyl macrogolglyceride (such as LABRAFIL® M 1944 CS, as available from Gattefossé (Saint-Priest, France)). In another aspect, the surface tension decreasing component may comprise a surfactant mixture. In a preferable aspect, the surface tension decreasing component comprises an oleoyl macrogolglyceride or a mixture of oleoyl macrogolglycerides.

The particular amount of surface tension decreasing component that constitutes an effective amount is dependent on the particular oil or oil mixture used in the formulation. Generally, depending on the carrier component selected for the formulation, particularly where the carrier component is an oil or oil mixture, it is necessary to select surfactants with compatible hydrophilic/lipophilic balance (HLBF) values to form the most stable emulsions.

While it is not practical to enumerate specific amounts of surface tension decreasing components for use with a variety of different carrier components, Table 1 below provides a general guide for providing the formulation of the invention.

TABLE 1

Typical composition of lipid formulation.

| Excipient | Content of formulation (% w/w) | | | | |
|---|---|---|---|---|---|
| | Type 1 | Type 2 | Type 3 | Type 4 | Type 5 |
| Oil | 100 | 40-100 | 40-100 | <20 | — |
| Surfactant HLB ≤ 12 | — | 0-60 | — | — | 0-20 |
| Surfactant HLB ≥ 12 | — | — | 20-40 | 20-50 | 30-80 |
| Hydrophilic co-solvent | — | — | 0-40 | 20-50 | 0-50 |

The formulation may optionally further comprise a viscosity regulating agent, such as a thickener or gelling agent. While the amount of the viscosity regulating agent used in the formulation is dependent on the carrier used in the formulation, the formulation generally comprises the viscosity regulating agent in an amount of from about 0.5 to about 10% by weight, preferably about 0.5 to about 7% by weight, more preferably about 1 to about 4% by weight, and most preferably about 4% by weight. Examples of viscosity regulating agents include, but are not limited to, cellulose and derivatives thereof, polysaccharides, carbomers, polyvinyl alcohol, povidone, colloidal silicon dioxide, cetyl alcohols, stearic acid, beeswax, petrolatum, triglycerides, lanolin, the like, or mixture thereof. A preferred viscosity regulating agent is colloidal silicon dioxide (such as ACROSIL 200®, as available from Degussa).

Optional Components

In another aspect of the invention, the formulation may optionally comprise a viscosity regulating agent in an amount of from about 0.5 to about 10% by weight, preferably about 0.5 to about 7% by weight, more preferably about 1 to about 4% by weight, and most preferably about 4% by weight. Preferably, the viscosity regulating agent comprises a thickener or gelling agent, such as cellulose and cellulose derivatives, polysaccharides, carbomers, polyvinyl alcohol, povidone, colloidal silicon dioxide, cetyl alcohols, stearic acid, beeswax, petrolatum, triglycerides and lanolin, or a mixture thereof. More preferably, the viscosity regulating agent is colloidal silicon dioxide.

In another aspect, the viscosity regulating agent may comprise a mixture of viscosity regulating agents. In a preferred aspect, the mixture of viscosity regulating agents together with an ointment base such as oleo gel or PEG-, lanolin alcohol-, or petrolatum-ointment and about 0.5 to about 40% (w/w) of lanolin, hydroxypropyl methylcellulose, petrolatum, PEG 300-6000, glyceryl monostearate, beeswax, or CARBOPOL® (Noveon, Inc).

| | Constituents % - wt | | |
|---|---|---|---|
| | Useful | Preferably | Preferred |
| Active | — | 0.2-0.6 | 0.2-4 |
| Carrier | 60-98 | 75-95 | 85-95 |
| Surfactant | 1-20 | 1-10 | 1-5 |
| Viscosity Builder | 0.5-10 | 0.5-7 | 1-4 |

Processing.

Generally, the formulation of the invention can be prepared very easily. The lipophilic carrier and surface tension decreasing component are filled into a stirrer vessel and about 75% of the viscosity regulating agent is mixed in. The active ingredient is added under stirring to obtain a homogenous dispersion of the active ingredient. Next, the formulation is adjusted to the necessary viscosity with the remainder of the viscosity regulating agent. The formulation is preferably filled into a preservative-free unit-dose container.

Because some hormones have lower levels of solubility in water, liberation from the formulation is the speed-limiting step for adsorption. It has been surprisingly found that the incorporation of a hormone drug such as testosterone in the oily formulation of the invention containing a suitable surfactant leads to physiologic serum levels and to a steady, sustained action of the hormone over time, as well as to increased levels in the CSF.

It is believed that the special release of the hormone is due to the oily carrier and because the formulation remains on the mucous membrane for a prolonged period of time due to its viscosity. Upon contact of the formulation with the humidity of the mucous membrane, precipitation of the active ingredient is hindered by the ability of the surface tension decreasing component to form oil drops containing the active ingredient. Thus, by adding a surface tension decreasing component to the formulation, the dissolution pattern of the active ingredient becomes more favorable and effective because there is no big variability in dissolution, which ensures bioequivalence.

Treatment.

The steroid hormone testosterone exerts its effects in tissues before or after testosterone is reduced by 5-alpha reductase to dihydrotestosterone (DHT). Since DHT has stronger binding properties than testosterone, DHT produces different actions in the body. As shown in FIG. 1, although the testosterone level in serum of hypogonadal men is comparable, application of the nasal gel of the invention results in a much lower level of DHT as compared to application of a dermal gel on the market. Formulations resulting in low levels of DHT are particularly desired because there is some evidence that DHT promotes cell growth in the prostate gland and is linked to promoting the spread and growth of prostate cancer cells.

The formulation described below in Table 2 was selected for treatment of hypogonadism because of the serum/CSF level achieved for the active ingredient but also because of skin care properties, such as moistening of the nasal membrane, which are important for long term applications.

TABLE 2

Representative Formulation

| Compound | Concentration | Delivery per nostril |
|---|---|---|
| Testosterone | 4% | ≈4 mg |
| Colloidal silicon dioxide | 4% | ≈4 mg |
| Oleoyl macrogol-glycerides | 4% | ≈4 mg |
| Castor oil | 88% | ≈88 mg |

In another aspect of the invention, the formulation according to the invention may also be processed into powder form, such as by lyophilization or spray-drying.

Figure 2:
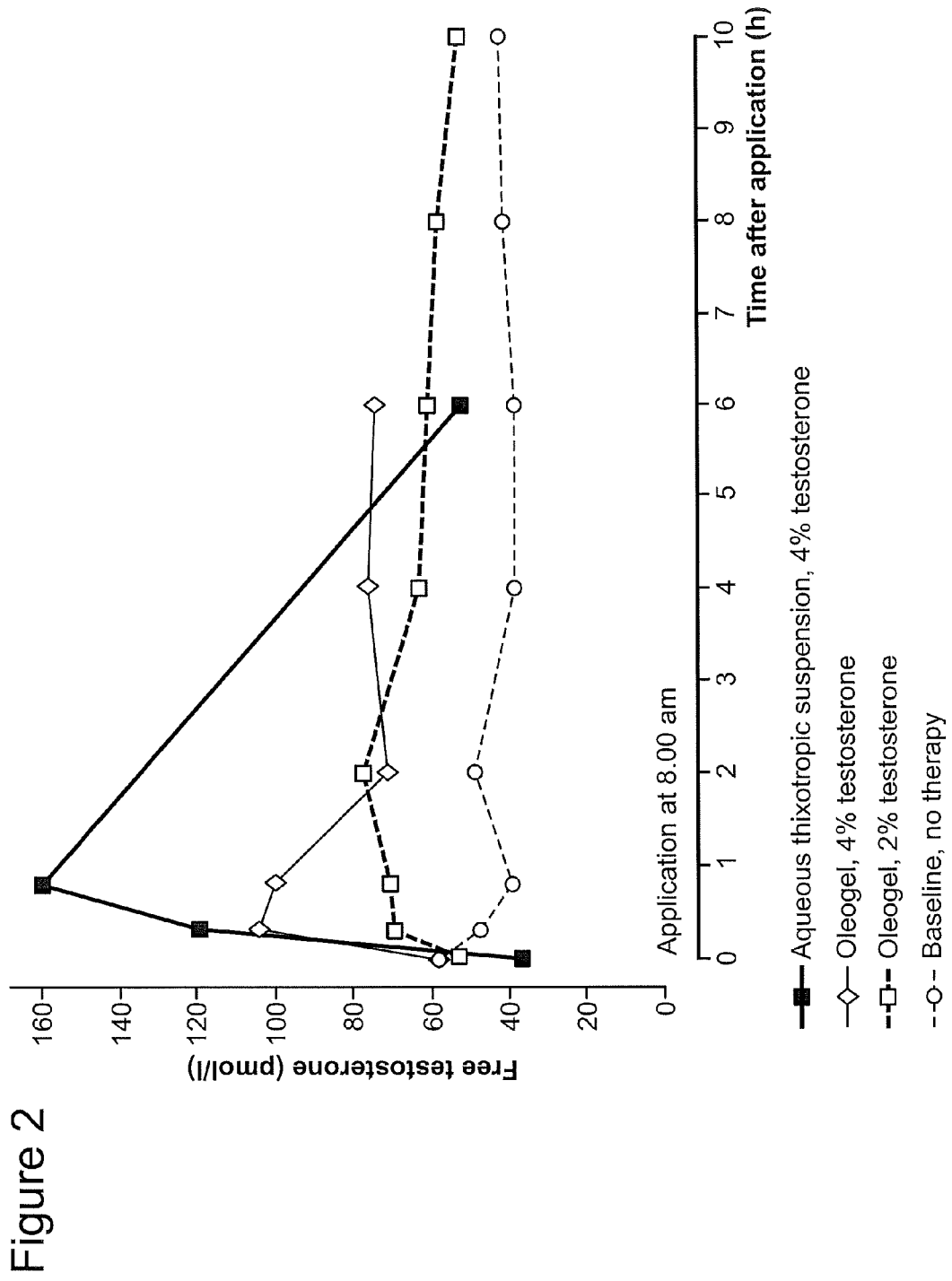
FIG. 2 shows the serum levels of free testosterone at baseline and after nasal application of testosterone.

Referring now to FIG. 2 and the preferred formulation containing testosterone described above in Table 2, $C_{max}$ is clearly decreased in the special formulation of the invention, which is desirable in view of toxicological considerations. Further the level of unbound testosterone is very constant over at least ten hours, which mimics the physiologic daily rhythm of testosterone release. The dotted line shows the serum level after application of one spray per nostril of the preferred formulation.

It can be concluded that the inventive formulation for nasal application is different from conventional formulations, especially those designed for sustained release, because the inventive formulation mimics the physiologic daily rhythm of testosterone release. The invention also avoids supra- and subnormal testosterone levels, which is easier for the patient to tolerate and, importantly, is suitable for hormone replacement therapy. As shown in FIG. 2 (upper line), a simple nasal spray containing testosterone is unsatisfactory in this sense.

Figure 3:
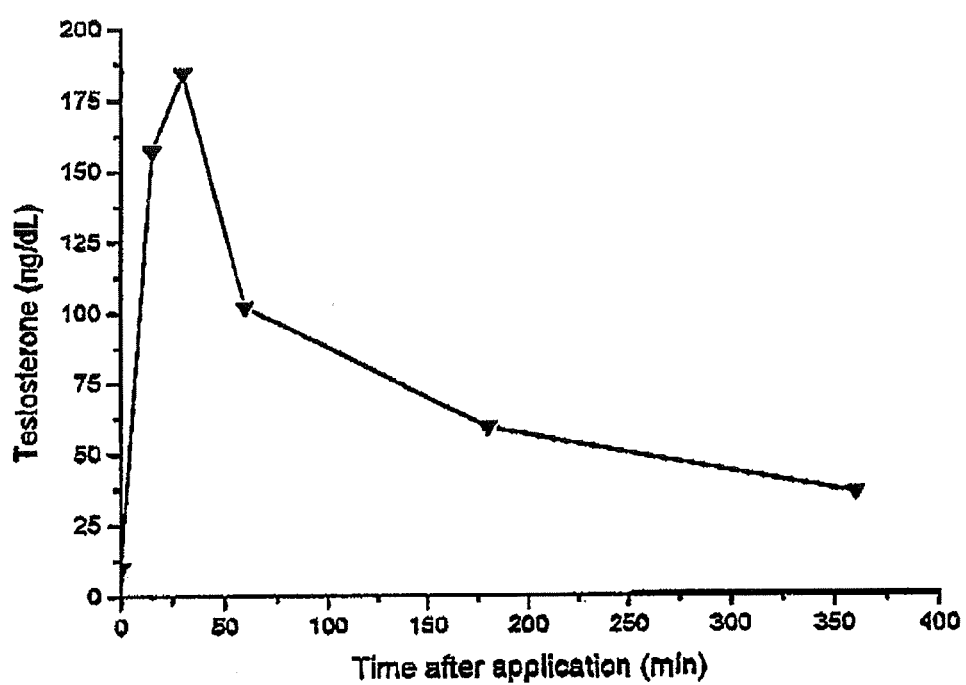
FIG. 3 shows the effect of a single nasal dose of 0.9 mg testosterone in women.

As shown in FIG. 3, application of testosterone in the inventive nasal gel formulation to women results in peak level ($C_{max}$) after about fifteen and before at least seventy-five minutes. Previous data regarding other forms of testosterone administration indicate: (1) a testosterone patch provides peak levels of testosterone at 24-36 hours (Advisory Committee Briefing Document, 2 Dec. 2004, P&G, p. 128); (2) a transdermal spray administered to the abdomen or forearm results in a peak level at 14-18 hours (Humberstone, A. J., et al., Poster No. P2-218; (3) a vaginal gel results in peak level at 5.5 hours (Apperloo et al.); and (4) an oral capsule of testosterone results in peak level at 5-7 hours (Houwing, N. S., et al., Pharmacotherapy 23(10): 1257-65 (2003)).

WORKING EXAMPLES

The following examples are intended to further illustrate, and not limit, embodiments in accordance with the invention.

Example 1

Nasal Administration of Testosterone to Women

Figure 4:
FIG. 4 shows the fMRI data indicating the brain response to emotional faces after nasal administration of testosterone.

The rapid and relatively high peak concentration of testosterone after application of testosterone was shown to correspond to a signal in the brain. Fourteen healthy, premenopausal women, between thirty-five and forty-five years of age during early follicular phase and who were not taking hormonal contraceptives, received the inventive nasal gel containing 0.9 mg testosterone or a placebo forty minutes before scanning. Scanning was done with functional magnetic resonance imaging (fMRI) using a 1.5 T Siemens Sonata MR scanner (TR 2.29 s, TE 30 ms, 3.5×3.5×3.5 mm voxels) to investigate the regional cerebral blood flow. During scanning, the subjects had to match the emotional expression with faces of different individuals expressing either anger or fear. As shown in FIG. 4, the fMRI data shows that application of the nasal testosterone gel formulation produces rapid effects on the neural emotion circuitry. Although not wishing to be bound by theory, it is believed that the rapid effects on the neural emotion circuitry are mediated by non-genomic mechanisms.

Previous data has shown that the amygdala response is important to sexual arousal. Karama et al., Hum. Brain. Mapp. 16:1-13 (2002), has shown that female sexual arousal is associated with increased amygdala activation and Baird et al., Ann. Neurol. 55: 87-96 (2004), has shown that increased sexual drive is associated with larger amygdala volume. As shown in FIG. 4, the nasally applied testosterone gel formulation leads to an amygdala response after not more than forty minutes. The fMRI results show that a single dose of nasal administration of the inventive formulation is able to restore the activation of amygdala region. The nasally applied testosterone gel formulation therefore is useful for the treatment of Female Sexual Dysfunction (FSD) or female sexual arousal disorder.

Figure 5:
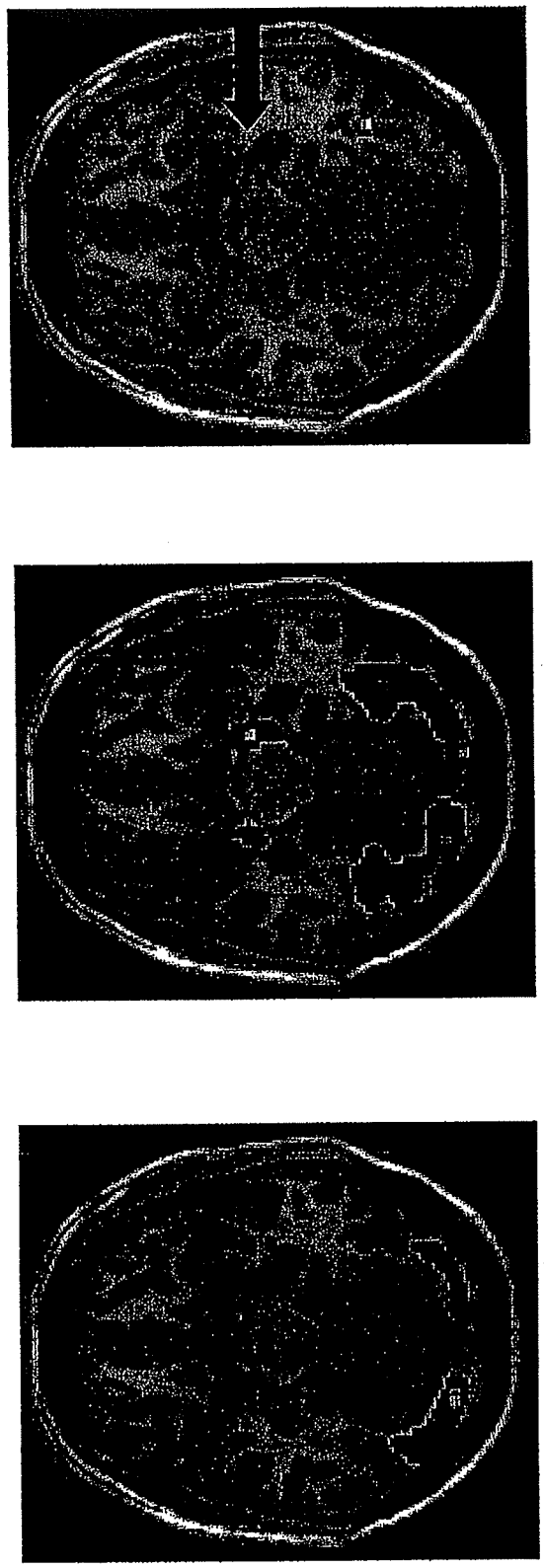
FIG. 5 shows the fMRI data indicating the brain response to emotional faces after nasal administration of placebo.

As shown in FIG. 5, young women between nineteen to thirty years of age have a higher amygdala response than that seen in middle-aged women between thirty-five to forty-five years of age when both groups are given placebos. A comparison of FIG. 4 with FIG. 5 demonstrates that treatment with the testosterone nasal gel of the invention increases the emotional reactivity of the middle-aged women to a level similar to that seen with the young women in the placebo group.

Figure 6:
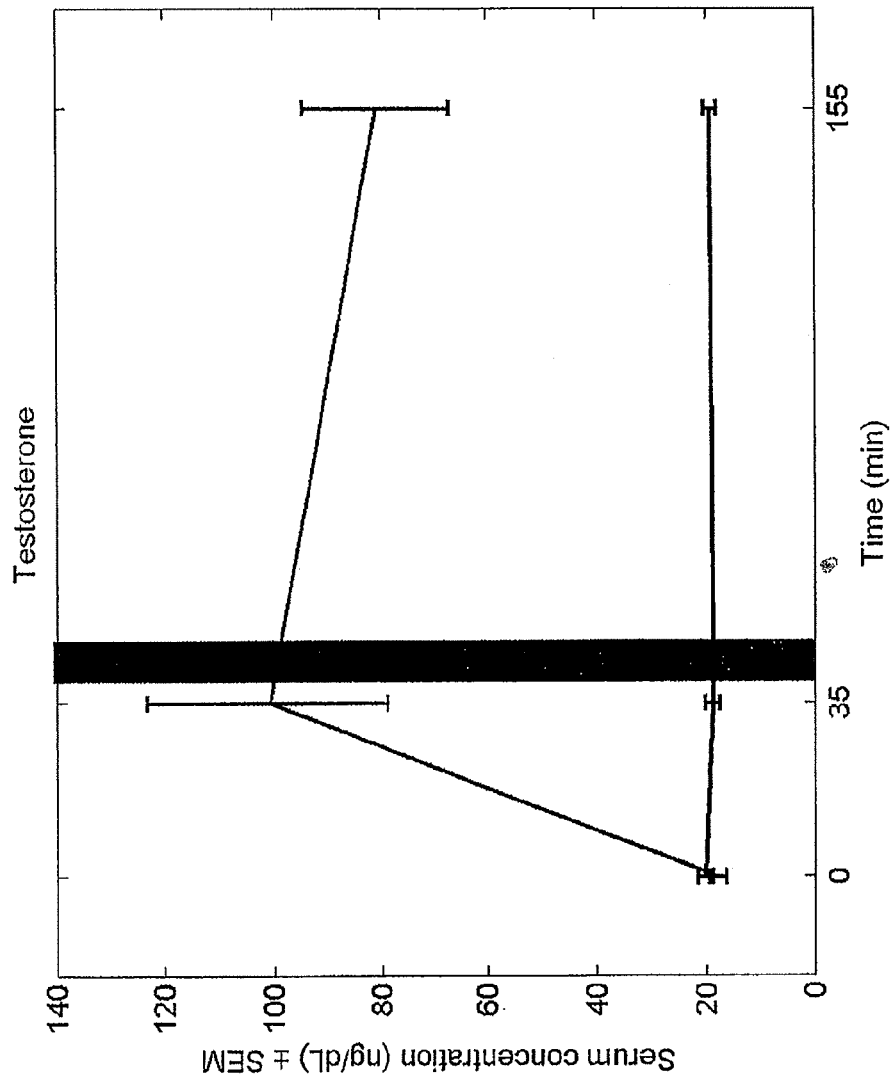
FIG. 6 shows the serum concentration of testosterone in women over time during fMRI.

In addition to the fast response seen in the brain, the nasal gel formulation also triggers a long lasting effect. Further fMRI data and serum concentration levels, as shown in FIG. 6, show that the response lasts for 2.5 hours. Therefore, both genomic and non-genomic signaling mechanisms can be assumed. Because it is not sufficient for a neurotherapeutic agent to cross the blood-brain barrier (the neurotherapeutic agent must also stay in the brain long enough to exert its action), a prolonged serum level is desirable for the action in the periphery.

It was also found that an intermittent nasal application of the inventive gel promotes female sexual proceptivity, which, for safety reasons, is extremely favorable in women.

Example 2

Effects of Nasal Administered Testosterone on the Sexual Behavior of Female Capuchin Monkeys (*Cebus apella*)

The objective of the study was to investigate the effects of nasal administered testosterone on the sexual behavior of female capuchin monkeys (*Cebus apella*).

Ten brown tufted capuchins (*Cebus apella*) were used as subjects as focal animals in this study. Animals were all adult females (>5 years old). All animals were weighted prior to and following the experimental procedures as described in Table 1.

TABLE 1

Weight of Female Capuchins Monkeys in the Noseafix Experiment.

| Female Number | Baseline Sept. 23 | Treat. 1 Sept. 30 | Treat. 1 Oct. 03 | Washout Oct. 08 | Treat. 2 Oct. 10 | Treat. 2 Oct. 13 |
| --- | --- | --- | --- | --- | --- | --- |
| 1 | 2.120 | 2.070 | 2.205 | 2.140 | 2.175 | 2.115 |
| 2 | 2.265 | 2.330 | 2.545 | 2.520 | 2.370 | 2.390 |
| 3 | 2.390 | 2.360 | 2.355 | 2.390 | 2.350 | 2.340 |
| 4 | 2.390 | 2.330 | 2.385 | 2.395 | 2.320 | 2.345 |
| 5 | 2.500 | 2.195 | 2.225 | 2.315 | 2.310 | 2.245 |
| 6 | 2.510 | 2.490 | 2.640 | 2.315 | 2.480 | 2.615 |
| 7 | 2.500 | 2.445 | 2.610 | 2.600 | 2.450 | 2.465 |
| 8 | 1.740 | 1.725 | 1.795 | 1.765 | 1.755 | 1.760 |
| 9 | 2.610 | 2.595 | 2.695 | 2.740 | 2.700 | 2.745 |
| 10 | 2.520 | 2.370 | 2.325 | 2.430 | 2.410 | 2.325 |

Females were housed in heterosexual pairs, see Table 2:

TABLE 2

| N° | Housing Condition | Females' Number | Females' Name |
| --- | --- | --- | --- |
| n = 4 | Family Groups (reproductive pair and offspring) | 2 | Rosa |
|  |  | 4 | Drica |
|  |  | 7 | Salomé |
|  |  | 9 | Chiquinha |
| n = 2 | Adult Male | 1 | Maneca |
|  |  | 6 | Cida |
| n = 2 | Adult male and young female | 3 | Mila |
|  |  | 8 | Salete |
| n = 2 | Adult male and one adult female | 5 | Delia |
|  |  | 10 | Aurora |

The ten subjects were assigned to the two groups based on age and on the housing condition. They never had experienced exogenous testosterone before. Females were randomly assigned to the treatment and placebo group, comprising five animals, see Table 3.

TABLE 3

Design of the Female Capuchin Groups in the Noseafix Experiment.

| Animal Number | Animal Name | Treatment 1 (A) (Sept. 09-Oct. 03) | Treatment 2 (B) (Oct. 09-Oct. 13) |
|---|---|---|---|
| (1) | Maneca | Placebo | Noseafix |
| (2) | Rosa | Placebo | Noseafix |
| (3) | Mila | Noseafix | Placebo |
| (4) | Drica | Placebo | Noseafix |
| (5) | Delia | Placebo | Noseafix |
| (6) | Cida | Noseafix | Placebo |
| (7) | Salomé | Noseafix | Placebo |
| (8) | Salete | Placebo | Noseafix |
| (9) | Chiquinha | Noseafix | Placebo |
| (10) | Aurora | Noseafix | Placebo |

The monkeys were housed and tested at the Primate Center of the University of Brasilia, Brazil, under natural light, temperature and humidity conditions. The Primate Center is located within the grounds of an ecological reserve, such that home cages are surrounded by nearby native tropical semideciduos gallery forest. Subjects were housed in the *Cebus* Colony room of the Primate Center, which contains two species of cebids: Brown tufted capuchins—*Cebus apella* and Squirrel monkeys—*Saimiri ustus*. The colony room consists of two rows of 6 cages (4 m length, 2, 9 width, ×2 m height, each cage respectively) consist of two concrete walls, separating adjacent cages, and a wire mesh front, back and ceiling forming an outdoor/semi-indoor housing system. Each cage consist of two concrete walls, separating adjacent cages, and a wire mesh front, back and ceiling forming an outdoor/semi-indoor housing system.

Each home cage contains a suspended wood nest-box, several wood perches at different heights, a food tray (where food bowl is placed) and a thick layer of natural dry leaves and twigs on the floor. Olfactory and acoustic contact is possible between all members of the colony, but not visual contact.

Food is provided once a day at 7:30 am., remaining in the home cages until 5:30 pm. The provisions include a variety of fresh fruits and vegetables. Dry pellets and fresh water are available ad libitum. Animals are weighted and clinically evaluated by a veterinary once a month.

The study was a randomized, double-blinded, cross-over with a non-treatment run-in. The experimental procedure was divided into 23 days in 4 consecutive phases:
Baseline=8 days (−7, −6, −5, −4, −3, −2, −1, 0)
Treatment 1 (A)=5 days (1 to 5)
Wash out=5 days (6 to 10)
Treatment 2 (B)=5 days (11 to 15)

The study started with a no-treatment run-in. In this study phase, the non-influenced (sexual) behavior of the female capuchin monkeys was observed and recorded as baseline. Behavioral observations were carried out daily during 23 experimental days (between 8 am and 5 pm). During all the phases, the behavior of the females' capuchin monkeys was individually observed throughout the day by four experienced observers. The behaviors were scored using a combination of continuous recording and instantaneous sampling (point samples every 7 minutes), (Martin and Bateson, 1986). The description of sexual behaviors is based on studies on capuchins sexual behavior, (Carosi et al., 1999; Carosi and Visalberghi, 2002). All behaviors were scored manually on spreadsheets and chronometers.

Each animal was observed four times a day (two sessions in the morning and two sessions in the afternoon). Each observation session lasted 14 min (7 min for instantaneous sampling and 7 min for continuous recording). The total amount of hours observed throughout the four phases of the experiment were 214.6.

Reliability for behavior identifications was assessed using data from three observations' days previous to the beginning of the study. Interaobserver (between the four observers) and intraobserver reliability were calculated as the sum of agreements between observers divided by the sum of disagreements. The concordance' index was up to 85%.

The behaviors observed were classified in sexual: eyebrow raising, mutual gaze, head cocking, chest rubbing, masturbation, extended arm(s), body touching mounting attempt, mounting, courtship, and non-sexual behaviors: resting, repetitive behavior, grooming, activity, and agonistic. Their operational definitions are presented in Table 4.

TABLE 4

Behavioral Definitions and Recording Techniques Used

| Behavior (recording technique) | Definition |
|---|---|
| Eyebrow raising (I) | F's eyebrows are raised up and backwards and the fur over the crown is flattened. |
| Mutual gaze | F and M maintain mutual eye contact for at least 2-3 s. It involves eyebrow raising. |
| Head cocking (I) | F's head is tilted to one side (approx. 45°). The head may gently change side every few seconds. |
| Chest rubbing (I) | F's hand(s) are slowly rubbed back and forth on the fur of its own chest. The movements are usually upward and/or downward and repeated several times in a row. |
| Masturbation (I) | F rubs its own genital with hands. |
| Extended arm(s) (CR) | F slowly moves/stretches one or both arms toward M, without contacting M. Individuals are in proximity usually seated, facing and looking at each other. |
| Body touching (CR) | F's hand gently reaches out and touches M's body for at least a few seconds. |
| Mounting attempt (CR) | M tries to mount F, but F moves away. |
| Mounting (CR) | M mounts F in a position which allows for copulation. Thrusting usually occurs. A mounting bout starts when M gains a mounting position and ends when it dismounts. Bouts can be isolated or form a mounting sequence. F may also mount M. |
| Courtship (CR) | F seeks the M attention or the observer attention. The courtship includes all the behaviors described for instantaneous sampling: eyebrow raising, mutual gaze, head cocking, chest rubbing and masturbation. |
| Resting (CR) | F is still on a substrate without doing anything else. |
| Stereotypy behavior (CR) | F goes, moves repeatedly to one place to another without any other behavior associated. |
| Grooming (CR) | F cleans its hair, another animal hair or it is cleaned by another animal. |
| Activity (CR) | It includes all the non-sexual female behaviors that were not described before such as foraging, playing, drinking, eating and moving. |
| Agonistic (CR) | Aggressive behavior including threat, chase way, grab with or without vocalization. |

* Abbreviations: I, instantaneous sampling (-s intervals); CR, continuous recording; F, female; M, male.

Measurements.

The following measurements were done during the study:
Baseline phase: Body weight
    Testosterone morning concentration
    Behavior Wash-out phase: Body weight
Testosterone morning concentration
Behavior
Treatment phases: Body weight
Testosterone morning concentration
Behavior The daily dose of the respective study drug was administered in the morning by study staff using the original recipient for a single dose. The test drug and the placebo were administered at the same interval time in the morning by the same experimenter in all days during the treatment 1 and 2. The drug was administered after the blood has been collected by the same experimenter in both nostrils of each animal.

The study staff filled out a treatment protocol for each animal and confirmed the administration with date and signature.

In order to obtain the blood samples during all the phases of experience, the animals were captured by a caretaker with the aid of a net, removed with leather gloves, anesthetized with isoflurano nasal and then transported to a table where the procedure was done. The order of capture of the females was maintained for all the days of the experiment. Time between the capture, blood collection and recovery of the females varies from 5 to 30 minutes depending on the animal.

Blood samples were drawn between 08:15 to 10:40 a.m. six times throughout the total time of experiment during the baseline, wash-out and treatment phases (Days=−5, 2, 5, 10, 12 and 15, respectively). The isoflurano 1 ml was administered nasally in a cotton ball placed at the nose of the animals until that sedation effect was observed. Once the animal is anesthetized, 1.5 ml of the venous blood was drawn from each female. On day $10^{th}$ we could not get a blood sample of the female number 4, Drica.

The transport of the analytical samples (plasma samples) from the Primate Center to the analytical laboratory at the Pharmacology Department at the University of Brasilia, was performed in thermo-isolated boxes contained dry ice. The temperature during the transport was not warmer than −20° C. Each blood sample containing heparin was immediately centrifuged at 2000 rpm for 10 minutes. The plasma was separated and put in duplicate test tubes labeled with the protocol number, study period, animal number, animal name, date and time of sampling. The test tubes with the blood were safely closed. The plasma samples were safely racked and immediately frozen for storage at −80° C.

Samples were stored in labeled tubes containing heparin as anticoagulant. The label of the blood collecting tubes contained information about protocol number, study period, animal number, animal name, date and time of sampling.

Phase 1: Baseline.

This first phase consisted of 8 consecutive days (from −7 to 0 day) where the baseline values of sexual and non-sexual female behaviors were recorded for 10 animals. During this phase, the non-influenced (sexual) behavior of the females' capuchin monkeys was individually observed through the day by 04 independent observers. The behaviors were scored using focal animal's continuous recording and focal instantaneous sampling methods. On the day −5, the first blood sample was collected for each female. After the blood has been collected, the animal was placed back into their home cage and released.

Phase 2: Treatment 1(A).

This phase consisted of 5 consecutive days (day 1 to day 5) with the nasal administration as single doses of 0.48 mg of testosterone (Noseafix®) 0.48 mg of testosterone (0.24 mg per nostril), once daily for 5 female capuchin monkeys (animal numbers 3, 6, 7, 9 and 10) as presented in Table 3. The 5 other females received gel for nasal administration with content identical to Noseafix. On day 2 and 5, blood samples were collected for the animals. Sexual and non-sexual behavior were recorded by the same observers of the previous phase for all days and according to the behavior categories described before. The blood samples were obtained using the same procedure described in the general description of protocol.

Phase 3: Wash Out.

During five consecutive days (day 6 to day 10), sexual and non-sexual behavior were recorded by the same observers of the previous phases using the same behavioral categories already described. On day $10^{th}$ for nine females we draw 1, 5 ml of venous blood. It was not possible to get a blood sample of the animal 4 on this day.

Phase 4: Treatment 2(B).

This phase was equal to the Treatment 1 except by the fact that the animals that got drug received placebo and viceversus. All the procedures to capture the animals, collect blood, administer the drug or placebo and recording the behavior were the same as described previously. On the days $12^{th}$ and $15^{th}$, new sample blood were taken from all the capuchin females.

Noseafix®.

Name of the drug: Noseafix® (0.48 mg of testosterone/vial)
Pharmaceutical form: gel for nasal administration
Content: active ingredient: testosterone
Excipients: according to the analytical certificate
Mode of administration: nasal, as single doses of 0.48 mg of testoterone (0.24 mg per nostril), once daily for 5 days
Manufacturer: HOLOPACK GmbH—Abtsgmünd/Germany for Mattern Research AG-Stans/Switzerland Noseafix® Placebo.

Name of the drug: Placebo
Pharmaceutical form: gel for nasal administration
Content: identical to the gel base of Noseafix®
Mode of administration: nasal, single dose (same volume as measured for Noseafix®), once daily for 5 days
Manufacturer: HOLOPACK GmbH—Abtsgmünd/Germany for Mattern Research AG-Stans/Switzerland Behavioral Analysis.

Behavioral raw data were transformed for the analysis as a function of the length of time of the observational sessions. Individually daily frequencies or durations were divided by the duration (in seconds) of each observational session. Thus, rates and percentages of time spent in each behavior were obtained. Daily scores of the behaviors sampled with the instantaneous technique were expressed as a proportion of the total number of point samples of the sessions.

Statistical Analysis
Data are expressed as the mean±SEM
Results are based in two-tailed statistical tests
Significance level was set at $p \leq 0.05$ Comparisons were done within each group to evaluate if the variables measured for each behavior were significantly modified by the treatment. With this purpose, we carried out one-way Analysis of Variance (ANOVA), taking each behavior as dependent variable, and the experiment's phase as independent variable, followed by post hoc analysis with Tukey's all-pair wise comparisons when applicable.

The results are presented separately for data collected using the Scan and the Continuous Recording methods.

Eyebrow Raising.

In female tufted capuchins "eyebrow raising", "touching and running", "nuzzling", and, to a lesser extent, "headcocking" are displays strongly correlated to the periovulatory phase and represent female proceptivity (Carossi, et al., 1999).

Figure 7:
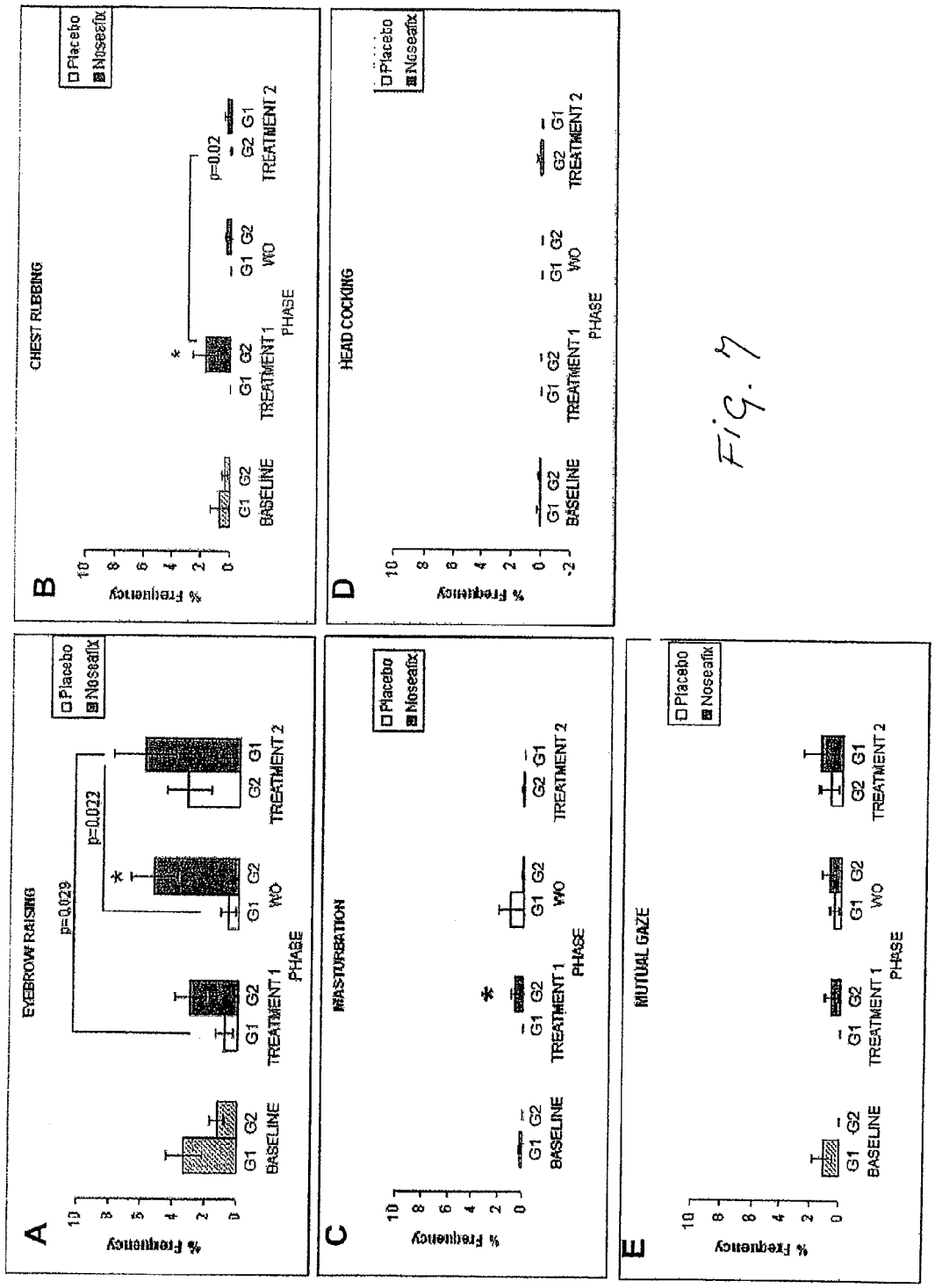
FIG. 7 Percentage (±SEM) of frequency of Eyebrow Raising (A), Chest Rubbing (B), Masturbation (C), Head Cocking (D) and Mutual Gaze (E), measured by instantaneous sampling in the different phases (Baseline, Treatment 1, Wash Out, Treatment 2) for the Group 1 (G1: Placebo-Noseafix) and Group 2 (G2: Noseafix-Placebo). *p<0.05 vs. baseline.

Statistical comparisons within Group 1 (Placebo in the treatment 1 phase—Noseafix in the treatment 2 phase) indicated significant differences between treatments $[F_{3, 366}=3.692, p=0.012]$ (see FIG. 7). Post hoc tests demonstrated differences between Treatment 1 and Treatment 2 [p=0.029], and between Wash-Out phase and Treatment 2 [p=0.022]. These results indicate that animals treated with Noseafix at treatment phase 2 showed increased frequency of "eyebrow raising" when compared to treatment phase 1 (placebo).

Also, comparisons within Group 2 (Noseafix-Placebo) treatments showed significant difference between phases $[F_{3, 454}=2.786, p=0.040]$. Post hoc analysis indicated an increase of the frequency of this behavior during the treatment phase 1 (Noseafix), although not significant, the Wash-Out phase when compared with Baseline [p=0.022] (FIG. 7A), and during the treatment phase 2 (Noseafix). It is interesting to note that these increases reach significance during the Wash-Out phase which could be interpreted as a long lasting effect of Noseafix.

Figure 8A:
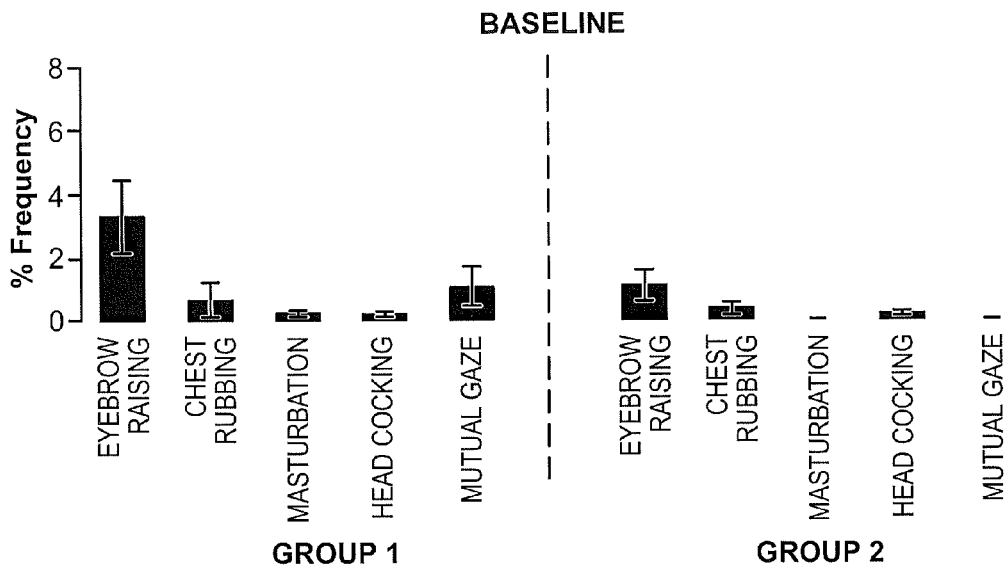
FIG. 8 Percentage (±SEM) of frequency in the Baseline (A), Treatment 1 (B), Wash Out (C) and Treatment 2 (D), of behaviors measured by instantaneous sampling (Eyebrow Raising, Chest Rubbing, Masturbation, Head Cocking and Mutual Gaze). For Group 1 (G1: Placebo-Noseafix) and Group 2 (G2: Noseafix-Placebo). *p<0.05 vs. Placebo.
Figure 8B:
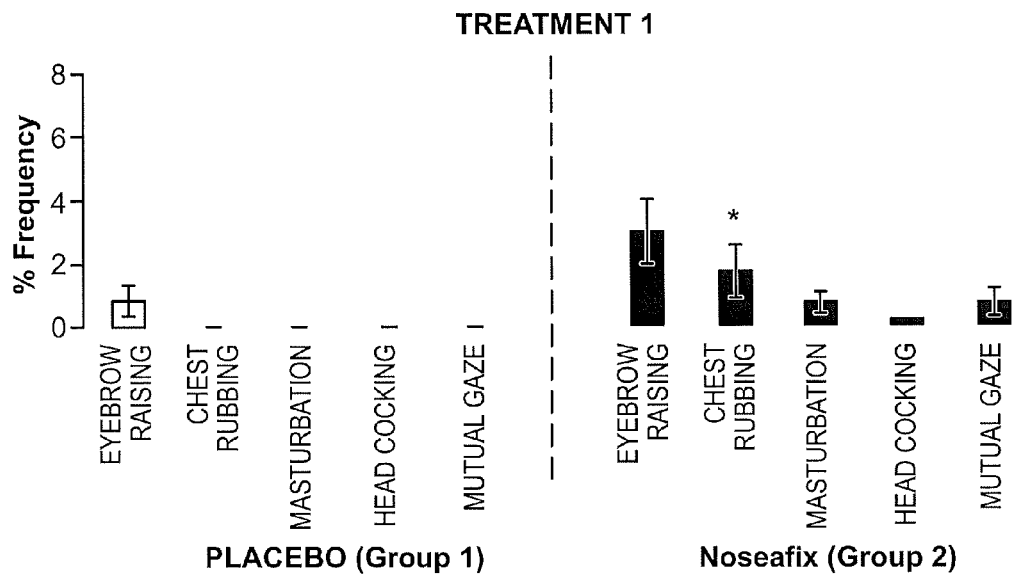
Figure 8C:
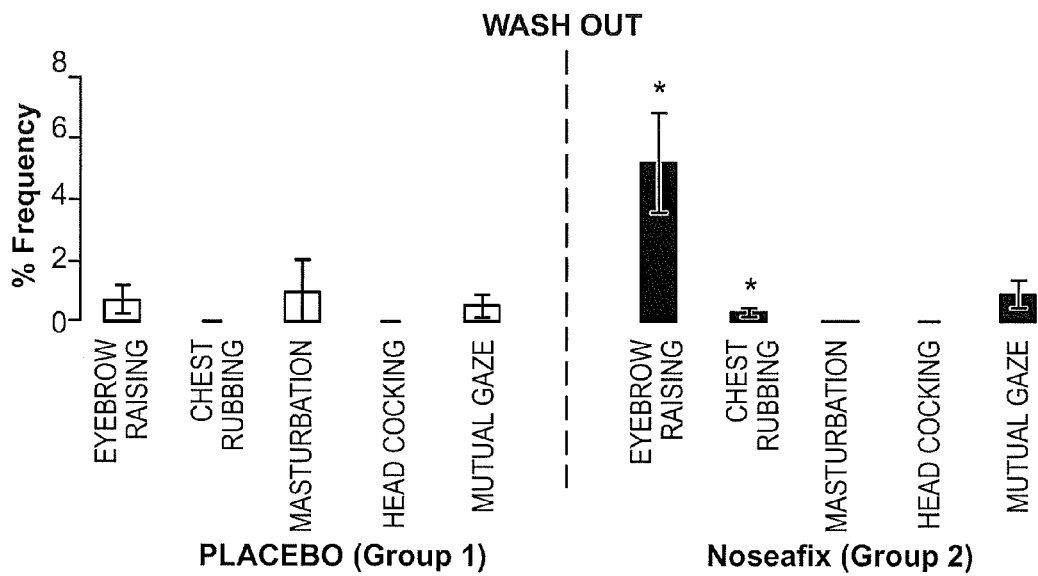
Figure 8D:
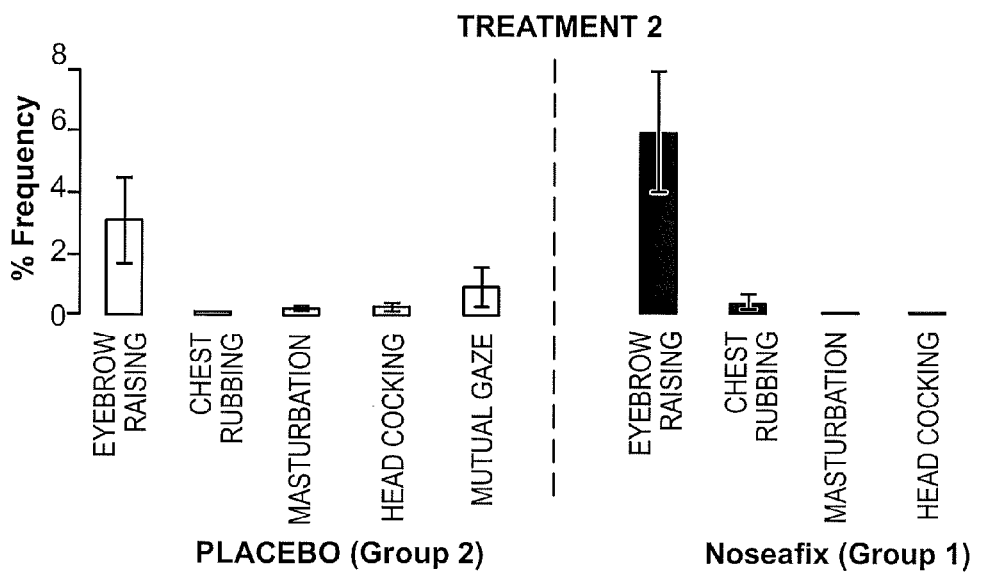

The frequency of eyebrow raising behavior was not different between groups during Baseline [t=1.691, p=0.093] (FIG. 8A), Treatment 1 [t=1.916, p=0.057] (FIG. 8B) and Treatment 2 [t=−1.140, p=0.256] (FIG. 8D). During the Wash-Out phase (FIG. 8C) the groups differed significantly [t=2.972, p=0.004], where Group 2 shown more frequently this behavior than the Group 1. These results suggest a long lasting effect of Noseafix treatment.

Chest Rubbing.

This behavior in Capuchin monkeys has been reported as one of the most prominent indication of female courtship (Carosi and Visalberghi, 2002). When multiple comparison within Group 2 (Noseafix-Placebo) were done, differences between phases were observed $[F_{3, 454}=3.439, p=0.017]$ (see FIG. 7B). Post hoc tests showed a significant increase during Treatment 1 phase when compared to both Baseline [p=0.049] and Treatment 2 [p=0.02]. Multiple comparisons within Group 1 did not show any significant difference due to the experimental phase $[F_{3, 366}=0.652]$ (FIG. 7B). These results indicate an effect of Noseafix treatment increasing the "chest rubbing" behavior. The placebo treatment had no effect at all. During Baseline [t=0.505, p=0.614] and Treatment 2 [t=−1.186, p=0.239], the frequency of the Chest Rubbing behavior (FIGS. 8A and 8D) did not differ between the groups. Group 2 had a greater frequency for this behavior compared to Group 1 in both Treatment 1 [t=−2.046, p=0.043] and Wash-Out [t=−2.811, p=0.006] phases (FIGS. 8B and 8C). These results again indicate an increase of "chest rubbing" by Noseafix. Moreover, the incidence of this behavior during the Wash-Out phase suggests a long lasting effect of the compound.

Masturbation.

Female capuchin monkeys perform mounting on adult males lasting from a few seconds up to 1-2 min. They usually stay on the male back in a position resembling that of an infant on its mother. However, the female can also take up a more proper mounting position, perform pelvic thrusts, and rub her genitals on the male's fur, as if masturbating. She can also perform a masturbation-like behavior by rubbing her genitals with the hands. This type of behavior typically occurs when the female is proceptive and she persistently solicits the male (Carosi and Visalberghi, 2002).

Multiple comparisons within each group did not find differences in Group 1 [F3, 366=0.822, p=0.482]. However, comparisons within Group 2 revealed differences due to phase [F3, 454=3.329, p=0.020]. Post hoc analysis indicated differences between Baseline and Treatment 1 [p=0.049], where during Treatment 1 an increase of the frequency of this behavior was found (FIG. 7C). This result suggests an effect of Noseafix treatment on the frequency of this behavior. No significant increase of masturbation was observed during treatment with placebo.

Comparisons for this behavior within phases between groups did not show significant differences [Baseline: t=1.467, p=0.145; Treatment 1: t=0.721, p=0.472; Wash-Out: t=0.925, p=0.358; Treatment 2: t=0.894, p=0.373] (FIG. 8A to 8D).

Head Cocking.

This behavior is characterized by the head tilted to one side (approximately 45°). The head may gently switch side every few seconds. The actor is constantly gazing at the recipient while cocking the head. This is performed by both sexes. Head cocking is performed by several prosimian and platyrrhine species during explorative activities, such as visual inspection of objects and unfamiliar persons (possibly to improve visual and auditory perception). The head cocking observed during capuchins' sexual interactions is unlikely to be related to the functions reported in other species (Carosi and Visalberghi, 2002).

Multiple comparisons within each group for the different phases, neither comparisons between the two groups within each phase showed any significant difference in the frequency of this behavior [Group 1: $F_{3, 366}=0.508, p=0.677$; Group 2: $F_{3, 454}=0.891, p=0.446$] (FIG. 7D), [Baseline: t=0.011, p=991; Treatment 1: t=−0.894, p=0.373; W-O: the behavior was not observed; Treatment 2: t=0.791, p=0.430] (FIG. 8A to 8D).

Mutual Gaze.

The monkeys may move repeatedly closer and farther apart while mutual gazing. Regardless of the distance between them, they try to regain mutual gaze. The mutual gaze usually lasts for several minutes, with occasional interruptions of a few seconds.

It is usually accompanied by one or all of the following behavioral patterns: eyebrow raising with grin and vocalizations, head cocking, and chest rubbing (Carosi and Visalberghi, 2002).

Comparisons for Mutual Gaze behavior between phases within each group did not show any significant difference [Group 1: $F_{3, 366}=0.837, p=0.474$; Group 2: $F_{3, 454}=1.264, p=0.268$] (FIG. 7E). Comparisons between groups within each phase also did not show significant differences for this behavior [Baseline: t=1.779, p=0.078; Treatment 1: t=−1.388, p=0.168; Wash-Out: t=−0.652, p=0.515; Treatment 2: t=−0.459, p=0.647] (FIG. 8A to 8D).

Grooming.

Figure 9A:
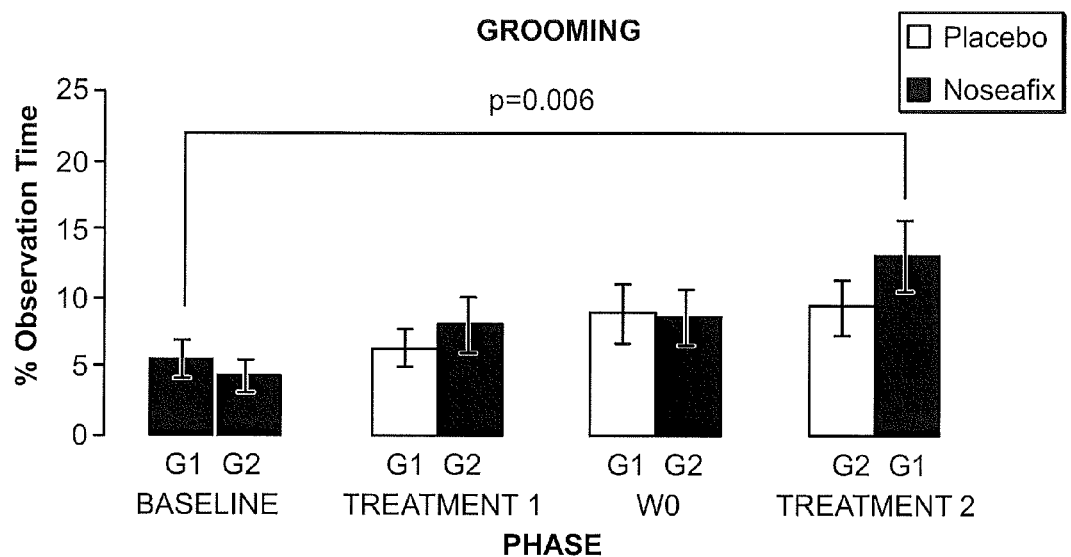
FIG. 9 Percentage (±SEM) of observation time of grooming (A), courtship (B) and agonistic behavior (C), measured by continuous recording in different phase (Baseline, Treatment 1, Wash Out, Treatment 2) for the Group 1 (G1: Placebo-Noseafix) and Group 2 (G2: Noseafix-Placebo). *p<0.05 vs. Baseline, Treatment 1 and Wash Out. The total Observation Time was: 224 minutes for Baseline and 140 minutes for each Treatment and Wash Out phase.

Differences between treatment phases were observed within Group 1 [$F_{3, 366}=3.246, p=0.022$]. Post hoc analysis demonstrated significant difference between Baseline and Treatment 2 [p=0.017], due to an increase of this behavior during Treatment 2 (when the subjects were under Noseafix treatment, see FIG. 9A). No such differences were observed within Group 2 [$F_{3, 454}=2.153, p=0.093$].

Comparisons within each phase did not show any difference in the time spent in Grooming between groups [Baseline: t=0, 7, p=0.485; Treatment 1: t=0.674, p=0.501; Wash-Out: t=0.138, p=0.89; Treatment 2: t=1.131, p=0.259] (FIG. 10A to 10D).

Courtship.

This category includes the following behaviors: extended arm(s), sexual display, body touching, courtship and mounting.

Figure 9B:
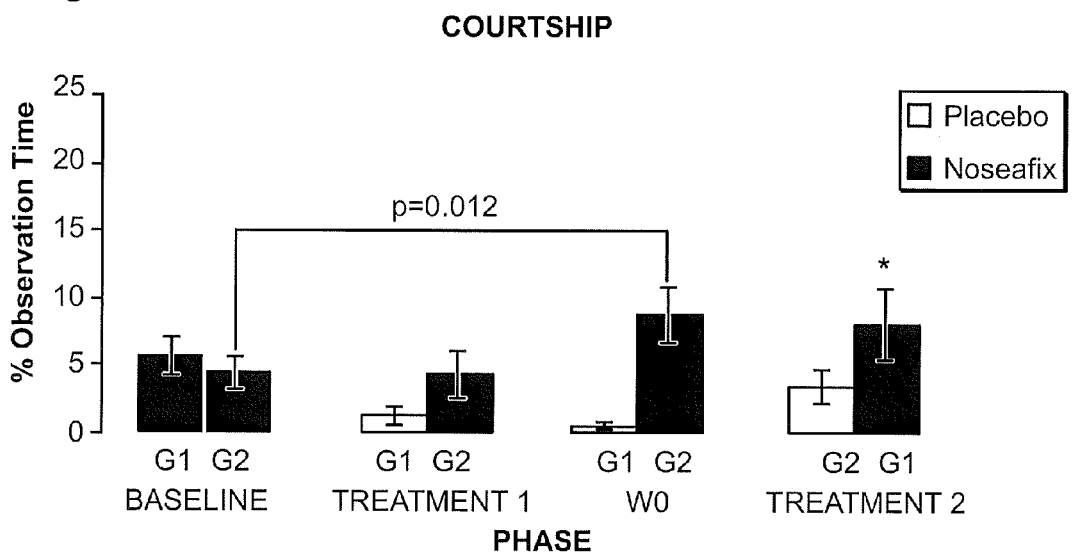

Multiple comparisons within each group between phases revealed significant differences for Group 1 [F3, 366=5.71, p=0.001] during Treatment 2 due to an increase of this category when compared to Baseline [p=0.03], Treatment 1 [p=0.005] and Wash-Out [0.001]; and for Group 2 [F3, 454=2.455, p=0.063] between Baseline and Wash-Out [p=0.043] (FIG. 9B). These results indicate that treatment with Noseafix increase courtship in female capuchin monkeys.

Figure 10A:
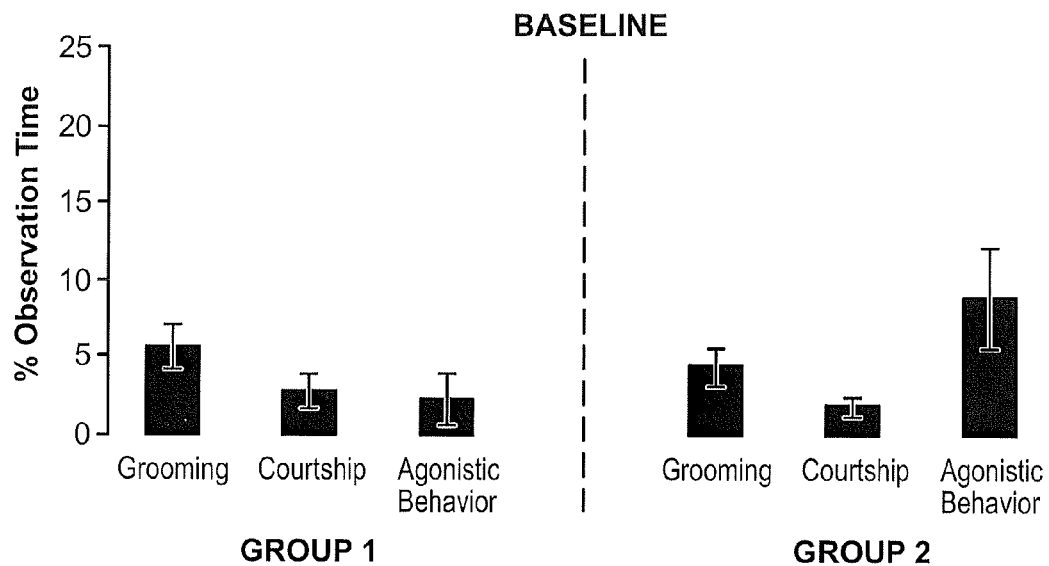
FIG. 10 Percentage (±SEM) of observation time in Baseline (A), Treatment 1 (B), Wash Out (C) and Treatment 2(D), of grooming, courtship and agonistic behavior, measured by continuous recording for Group 1 (G1: Placebo-Noseafix) and Group 2 (G2: Noseafix-Placebo). *p.<0.05 vs. Placebo. The total Observation Time was: 224 minutes for Baseline and 140 minutes for each Treatment and Wash Out phase.
Figure 10B:
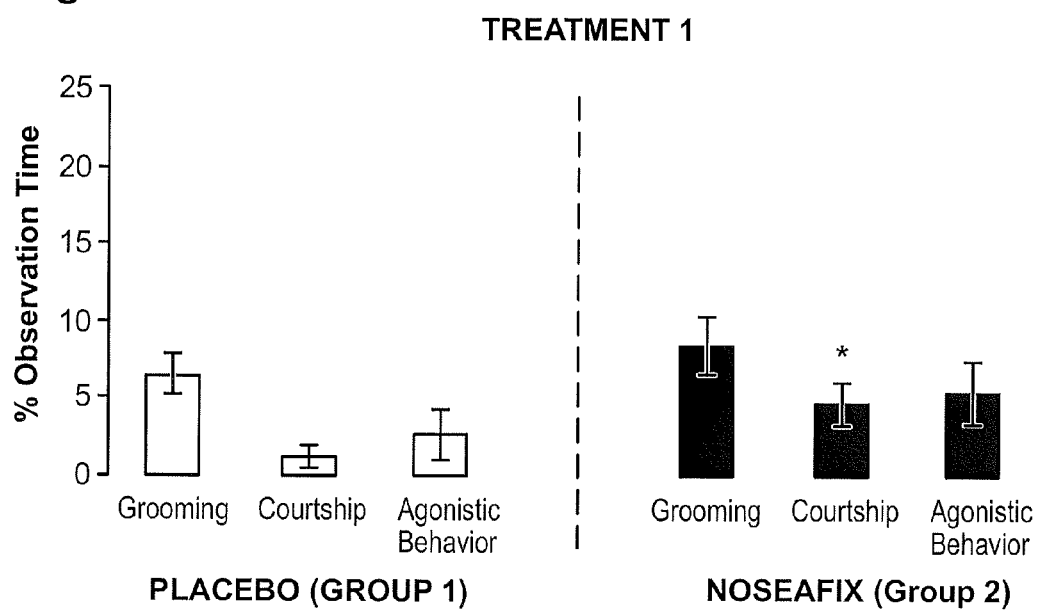
Figure 10C:
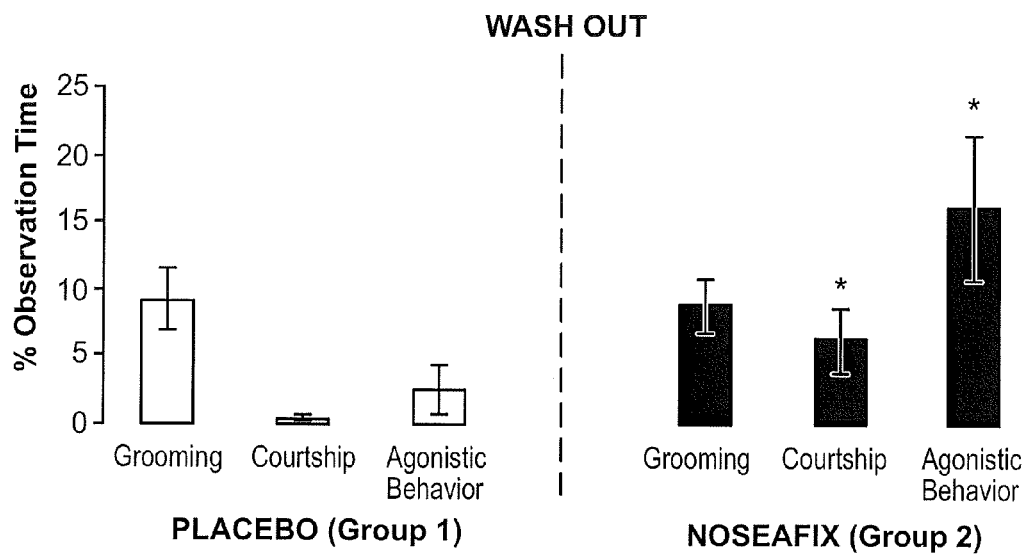

Comparisons of the time spent in courtship behaviors within each phase between groups shown significant differences during Treatment 1 [t=−2.007, p=0.047] and during Wash-Out [t=−3.08, p=0.003]. In both situations Group 2 spent more time than Group 1 (FIGS. 10B and 10C). During Baseline [t=0.975, p=0.33] and Treatment 2 [t=−1.654, p=0.101] no differences were observed between groups (FIGS. 10A and 10C).

Stereotypy.

Differences in the time spent in stereotyped behavior between phases within each group were not found [Group 1: F3, 366=1.878, p=0.133; Group 2: F3, 454=0.549, p=0.649] (Data not shown in figures).

Comparisons between groups within each phase demonstrated that Group 1 shown significantly higher percentage of time in this behavior than Group 2 in all the phases [Baseline: t=3.138, p=0.002; Treatment 1: t=3.538, p=0.001; Wash-Out: t=4.379, p<0.001; Treatment 2: t=−3.188, p=0.002] (Data not shown in figures).

Agonistic Behavior. (Chase Away).

Figure 9C:
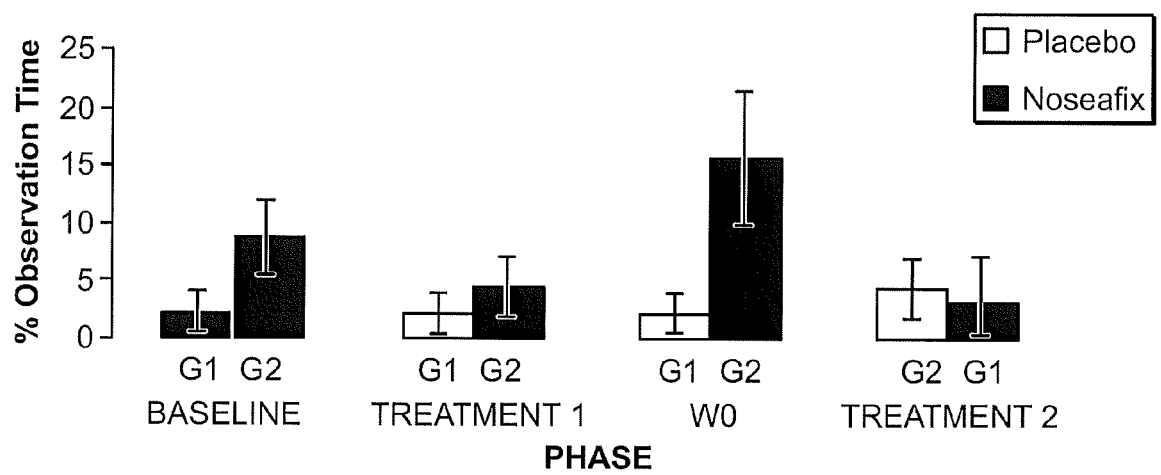

Multiple comparisons between phases within each group did not show significant differences in the observation time [Group 1: F3, 366=0.079, p=0.971; Group 2: F3, 454=1.703, p=0.166] (FIG. 9C).

Figure 10D:
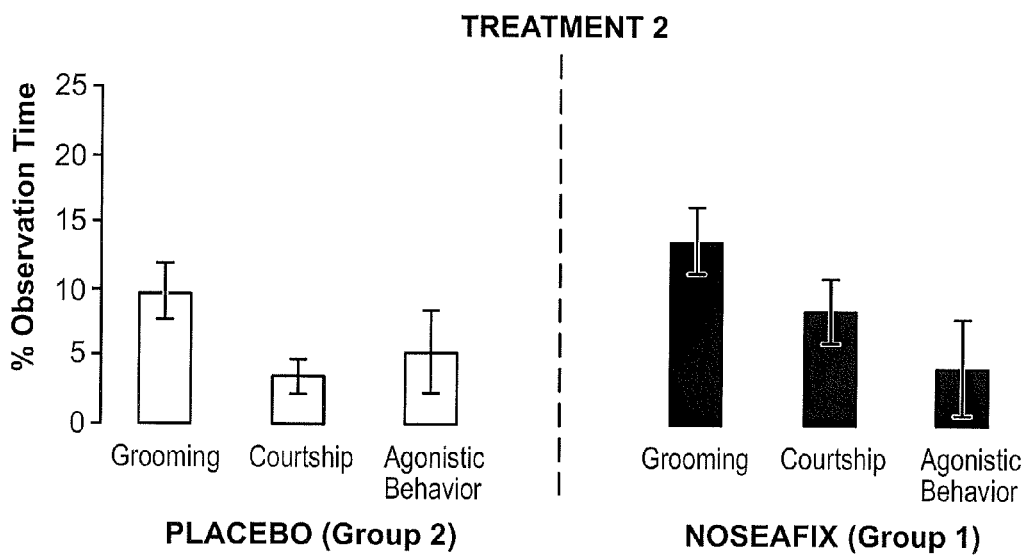

Comparisons of Agonistic Behavior within each phase between groups shown significant difference between them during the Wash-Out phase [t=−2.356, p=0.02], where the Group 2 shown more agonistic behavior than Group 1 (FIG. 10C). For the remaining phases significant differences were not observed [Baseline: t=−1.719, p=0.087; Treatment 1: t=−0.859, p=0.391; Treatment 2: t=0.265, p=0.792] (FIGS. 10A, 10B and 10D). It is worth to mention that this Chase Away behavior was observed only in one animal, although during a long time. It is not possible to be sure that this behavior observed during the Wash-Out period was elicited by the effect of testosterone (Noseafix) administered during treatment 1 phase (long lasting effect). However, it seems not likely since in capuchin monkeys, high levels of testosterone were not associated with aggressive behavior (Lynch, et al., 2002).

Figure 11:
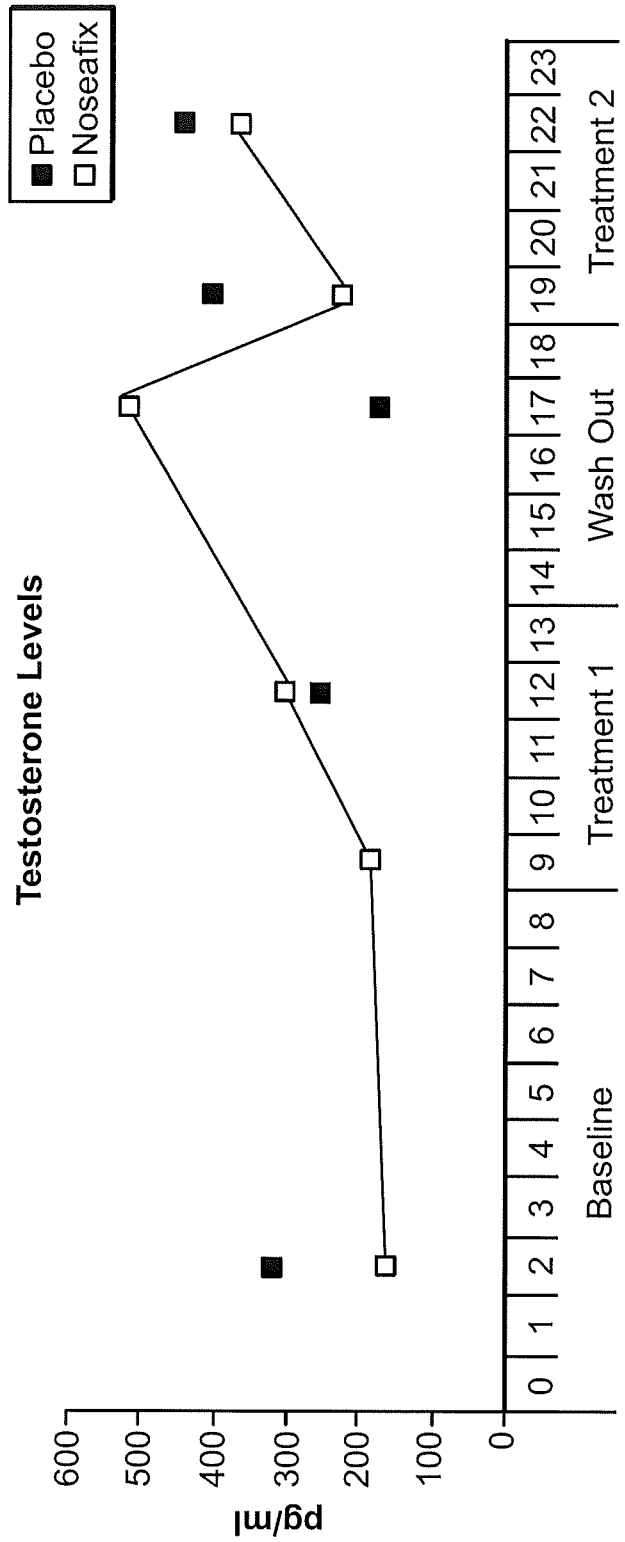
FIG. 11 shows the plasma testosterone levels in different phases of the study for the animals treated with placebo and the product Noseafix.

FIG. 11 shows the plasma testosterone levels in different phases of the study for the animals treated with placebo (blue squares) and Noseafix (red squares). As can be observed, the administration of Noseafix induced an increase in plasma testosterone level. It is interesting to observe that the high magnitude effect was observed when the animals were at the Wash-Out phase. This effect fits perfectly with the higher frequency of sexual arousal behaviors observed during the Wash-Out phase. Therefore, behavioral and plasma testosterone level shows a close relationship.

The two yellow squares in the Figure—Treatment 2 phase, illustrates the "possible" residual effect of Noseafix treatment during Treatment 1 phase. It would be interesting in other study to introduce a second Wash-Out phase (after treatment 2) in order to confirm this residual (long lasting) effects of Noseafix treatment on plasma testosterone levels and the proceptivity of female capuchin monkeys.

In summary, the results obtained indicate that administration of Noseafix seem to promote female sexual proceptivity in the tufted capuchin monkey (*Cebus apella*), which characterizes this species mating system. These effects are in close relationship to the plasma testosterone levels measured during this study. The following aspects summarize the major findings and the results that corroborate this conclusion:

The frequency of Eyebrow Raising, Chest Rubbing and Masturbation were enhanced by the administration of Noseafix. These behaviors are an indicative of female's sexual solicitation and are frequent displayed during the preiovulatory period (FIG. 1). It is important to mention that none of these behaviors were significantly observed in animals under placebo administration. Therefore, the females' proceptivity can not be related to the natural ovulatory cycle, although we can not rule out a possible interaction between Noseafix and ovulatory cycle in some animals. In order to exclude this possibility would be necessary to conduct another experiment in females where the natural cycle is blocked by the administration of a contraconceptive drug.

The female sexual appetitive activities such as invitational patterns and active initiative in approaching, investigating, and sexually soliciting the male were only observed in animals under Noseafix treatment (FIGS. 7 to 10). It is worth to mention that some of these behaviors were also observed during the Wash-Out phase, but only for the animals that have received Noseafix before. Therefore, it is possible that Noseafix has a long lasting effect. Since we did not do a PK study, it is not possible to know how long are the Noseafix effects in capuchin monkeys. Moreover, a second Wash-Out phase, after Treatment 2, would be interesting to observe possible occurrence of sexual display behaviors in animals treated with Noseafix during Treatment 2 phase. The compound tested did not exert a significant effect upon the frequency of exploratory activity or stereotyped behaviors in the monkeys tested. Therefore, the effects of Noseafix were not due to changes in the subject's level of activity.

The features disclosed in the foregoing description, in the claims and/or in the drawings may, both separately and in any combination thereof, be material for realizing the invention in diverse forms thereof.

I claim:

1. A method of testosterone replacement therapy comprising the step of nasally administering to a patient in need of such treatment an effective amount of a testosterone gel formulation comprising
   a) testosterone;
   b) at least one lipophilic or partly lipophilic carrier; and
   c) a compound or a mixture of compounds having surface tension decreasing activity.

2. A method according to claim 1, wherein said lipophilic carrier comprises an oil.

3. A method according to claim 2, wherein said oil is a vegetable oil.

4. A method according to claim 3, wherein said vegetable oil is castor oil.

5. A method according to claim 4, wherein the castor oil is hydrogenated.

6. A method according to claim 3, wherein said vegetable oil is soybean oil.

7. A method according to claim 3, wherein said vegetable oil is sesame oil.

8. A testosterone gel formulation according to claim 3, wherein said vegetable oil is peanut oil.

9. A method according to claim 2, wherein said lipophilic carrier comprises an oil mixture.

10. A method according to claim 2, wherein the oil is present in an amount from about 30% to about 98% by weight of the testosterone gel formulation.

11. A method according to claim 1, wherein said lipophilic carrier comprises a fatty acid ester.

12. A method according to claim 11, wherein the fatty acid ester is ethyloleat.

13. A method according to claim 11, where the fatty acid ester is oleyloleat.

14. A method according to claim 1, wherein said lipophilic carrier comprises isopropylmyrisate.

15. A method according to claim 1, wherein said lipophilic carrier comprises medium chain triglycerides.

16. A method according to claim 1, wherein said lipophilic carrier comprises glycerol esters of fatty acids.

17. A method according to claim 1, wherein said lipophilic carrier comprises polyethylene glycol.

18. A method according to claim 1, wherein said lipophilic carrier comprises phospholipids.

19. A method according to claim 1, wherein said lipophilic carrier comprises white soft paraffin.

20. A method according to claim 1, wherein said compound or a mixture of compounds having surface tension decreasing activity comprise (a) at least one surfactant selected from the group consisting of lecithin, a fatty acid ester and mixtures thereof, (b) at least one humectant selected from the group consisting of sorbitol, glycerine, polyethylene glycol and a macrogol glycerol fatty acid ester and mixtures thereof, and (c) mixtures thereof.

21. A method according to claim 1, wherein said compound or a mixture of compounds having surface tension decreasing activity comprises an oleoyl macrogolglyceride or a mixture of oleoyl macrogolglycerides.

22. A method according to claim 20, wherein said compound or a mixture of compounds having surface tension decreasing activity is present within the testosterone gel formulation in an amount of from about 1% to about 20% by weight of the testosterone gel formulation.

23. A method according to claim 1, further comprising a viscosity regulating agent.

24. A method according to claim 23, wherein said viscosity regulating agent comprises a thickener or gelling agent selected from the group consisting of cellulose and cellulose derivatives, polysaccharides, carbomers, polyvinyl alcohol, povidone, colloidal silicon dioxide, cetyl alcohols, stearic acid, beeswax, petrolatum, triglycerides, lanolin and mixtures thereof.

25. A method according to claim 23, wherein said viscosity regulating agent is colloidal silicon dioxide.

26. A method according to claim 23, wherein the viscosity regulating agent is present within the testosterone gel formulation in an amount of from about 0.5% to about 10% by weight of the testosterone gel formulation.

27. A method according to claim 1, wherein said testosterone is present within the testosterone gel formulation in an amount of from about 0.2% to about 6% by weight, of the testosterone gel formulation.

28. A method according to claim 1, wherein said testosterone is introduced into the testosterone gel formulation as microparticles.

29. A method according to claim 1, wherein said testosterone is introduced into the testosterone gel formulation as nanoparticles.

30. A method according to claim 1, wherein said testosterone is introduced into the testosterone gel formulation as liposomes.

31. A method according to claim 1, wherein said testosterone is introduced into the testosterone gel formulation as bilayer vesicles.

32. A method according to claim 1, wherein said testosterone is introduced into the testosterone gel formulation as micelles.

33. A method according to claim 1, wherein testosterone gel formulation provides for the controlled release of said testosterone into the systemic circulation after nasal application.

34. A method according to claim 33, wherein the testosterone gel formulation provides for sustained serum levels of said testosterone.

35. A method according to claim 33, wherein said testosterone is maintained at a serum level greater than baseline for at least 6 hours following nasal administration.

36. A method according to claim 35, wherein the testosterone serum level is achieved after one application per nostril of the testosterone gel formulation.

37. A method according to claim 35, wherein the level of unbound testosterone is similar to the physiologic daily rhythm of testosterone release.

38. A method according to claim 37, wherein the level of unbound testosterone is constant for at least about 6 hours following nasal administration.

39. A method according to claim 1, wherein the testosterone gel formulation is provided in a device capable of delivering multiple, individual doses of the testosterone gel formulation.

40. A method according to claim 2, wherein the oil is present in an amount of from about 60% to about 98% by weight of the testosterone gel formulation.

41. A method according to claim 2, wherein the oil is present in an amount of from about 75% to about 95% by weight of the testosterone gel formulation.

42. A method according to claim 2, wherein the oil is present in an amount of from about 85% to about 95% by weight of the testosterone gel formulation.

43. A method according to claim 2, wherein the oil is present in an amount of about 90% by weight of the testosterone gel formulation.

44. A method according to claim 20, wherein said compound or a mixture of compounds having surface tension decreasing activity is present within the testosterone gel formulation in an amount of from about 1% to about 10% by weight of the testosterone gel formulation.

45. A method according to claim 20, wherein said compound or a mixture of compounds having surface tension decreasing activity is present within the testosterone gel formulation in an amount of from about 1% to about 5% by weight of the testosterone gel formulation.

46. A method according to claim 20, wherein said compound or a mixture of compounds having surface tension decreasing activity is present within the testosterone gel formulation in an amount of about 4% by weight of the testosterone gel formulation.

47. A method according to claim 23, wherein the viscosity regulating agent is present within the testosterone gel formulation in an amount of from about 0.5% to about 7% by weight of the testosterone gel formulation.

48. A method according to claim 23, wherein the viscosity regulating agent is present within the testosterone gel formulation in an amount of from about 1% to about 4% by weight of the testosterone gel formulation.

49. A method according to claim 23, wherein the viscosity regulating agent is present within the testosterone gel formulation in an amount of about 4% by weight of the testosterone gel formulation.

50. A method according to claim 33, wherein said testosterone is maintained at a serum level greater than baseline for at least about 8 hours following nasal administration.

51. A method according to claim 33, wherein said testosterone is maintained at a serum level greater than baseline for at least about 10 hours following nasal administration.

52. A method according to claim 37, wherein the level of unbound testosterone is constant for at least about 8 hours following nasal administration.

53. A method according to claim 37, wherein the level of unbound testosterone is constant for at least about 10 hours following nasal administration.

54. A method of testosterone replacement therapy comprising the step of nasally administering to a patient in need of such treatment an effective amount of a testosterone gel formulation comprising
   a) testosterone;
   b) at least one lipophilic or partly lipophilic carrier in an amount from about 60% to about 98% by weight of the testosterone gel formulation;
   c) a compound or a mixture of compounds having surface tension decreasing activity in an amount from about 1% to about 20% by weight of the testosterone gel formulation; and
   d) a viscosity regulating agent in an amount from about 0.5% to about 10% by weight of the testosterone gel formulation.

55. A method of testosterone replacement therapy comprising the step of nasally administering to a patient in need of such treatment an effective amount of a testosterone gel formulation comprising
   a) testosterone;
   b) castor oil in an amount from about 60% to about 98% by weight of the testosterone gel formulation;
   c) an oleoyl macrogolglyceride or a mixture of oleoyl macrogolglycerides in an amount from about 1% to about 20% by weight of the testosterone gel formulation; and
   d) colloidal silicone dioxide in an amount from about 0.5% to about 10% by weight of the testosterone gel formulation.

* * * * *